US005650282A

United States Patent [19]
Keating et al.

[11] Patent Number: 5,650,282
[45] Date of Patent: Jul. 22, 1997

[54] DIAGNOSIS OF WILLIAMS SYNDROME

[75] Inventors: Mark T. Keating; Mark F. Leppert, both of Salt Lake City, Utah; Colleen A. Morris, Las Vegas, Nev.

[73] Assignee: The University of Utah Research Foundation, Salt Lake City, Utah

[21] Appl. No.: 474,021

[22] Filed: Jun. 7, 1995

Related U.S. Application Data

[63] Continuation of Ser. No. 41,576, Apr. 5, 1993, abandoned.
[51] Int. Cl.$^6$ .............................. C12Q 1/68; C12P 19/34; C07H 21/04; C12N 15/00
[52] U.S. Cl. .............................. 435/6; 435/91.1; 435/270; 435/968; 436/94; 536/23.5; 536/24.31; 536/23.1; 536/24.33; 935/78
[58] Field of Search .............................. 435/6, 91.1, 270, 435/948; 436/94; 536/23.1, 23.5, 24.31, 24.33; 935/77, 78

[56] References Cited

PUBLICATIONS

Curran et al., "The Elastin Gene is Disrupted by a Translocation Association with Supravalvular Aortic Stenosis," cell, vol. 73, pp. 159–168. Apr. 9, 1993.
Bashir, M.M. et al. (1989). "Characterization of the Complete Human Elastic Gene," *J. Biol. Chem.*, 264:8887–8891.
Curren, M.E. et al. (1993). "The Elastin Gene Is Disrupted by a Translocation Associated with Supravalvular Aortic Stenosis," *Cell* 73:159–168.
Ewart, A.K. et al. (1993). "A human vascular disorder, supravalvular aortic stenosis, maps to chromosome 7," *Proc. Natl. Acad. Sci. USA* 90:3226–3230.
Fazio, M.J. et al. (1991). "Human Elastic Gene: New Evidence for Localization to the Long Arm of Chromosome 7," *Am. J. Hum. Genet.* 48:696–703.
Fazio, M.J. et al. (1988). "Cloning of Full–length Elastin cDNAs from a Human Skin Fibroblast Recombinat cDNA Library: Further Elucidation of Alternative Splicing Utilizing Exon–specific Oligonucleotides," *J. Investigative Dermatology* 91:458–464.
Indik, Z. et al. (1987). "Alternative splicing of human elastic mRNA indicated by sequence analysis of cloned genomic and complementary DNA," *Proc. Natl. Acad. Sci. USA* 84:5680–5684.
Indik, Z. et al. (1987). "Structure of the 3' Region of the Human Elastin Gene: Great Abundance of Alu Repetitive Sequences and Few Coding Sequences," *Connective Tissue Research* 16:197–211.
O'Connor, W. et al. (1985). "Supravalvular Aortic Stenosis," *Arch. Pathol. Lab. Med.* 109:179–185.
Perou, M. (1961). "Congenital Supravalvular Aortic Stenosis," *Arch. Pathol.* 71:113–126.
Rosenbloom, J. et al. (1991). "Elastin Genes and Regulation of Their Expression," *Critical Reviews in Eukaryotic Gene Expression* 1:145–156.
Sandberg, L. et al. (1981). "Elastin structure, biosynthesis, and relation to disease states," *N. Engl. J. Med.* 304:566–579.
Tromp, G. et al. (1991). "A to G polymorphism in ELN gene," *Nucl. Acids Res.* 19:4314.
Uitto, J. et al. (1991). "Molecular biology and pathology of human elastin," *Biochem. Soc. Trans.* 19:824–829.
Yeh, H. et al. (1987). "Sequence variation of bovine elastin mRNA due to alternative splicing," *Coll. Relat. Res.* 7:235–247.
Yoon, K. et al. (1985). "Analysis of the 3' region of the sheep elastin gene," *Arch. Biochem. Biophys.* 241: 684–691.

*Primary Examiner*—Bradley L. Sisson
*Attorney, Agent, or Firm*—Venable, Baetjer, Howard & Civiletti, LLP

[57] ABSTRACT

The invention relates to the identification of the molecular basis of supravalvular aortic stenosis (SVAS) and Williams syndrome. More specifically, the invention has identified that elastin causes or is involved in the pathogenesis of SVAS and Williams syndrome. Molecular variants of the elastin gene contribute to SVAS and Williams syndrome. The analysis of the elastin gene will provide an early diagnosis of subjects with SVAS and Williams syndrome. The diagnostic method comprises analyzing the DNA sequence of the elastin gene of an individual to be tested and comparing it with the DNA sequence of the native, non-variant elastin gene. In a second embodiment, the elastin gene of an individual to be tested is screened for mutations associated with SVAS or Williams syndrome. Presymptomatic diagnosis of SVAS and Williams syndrome will enable practitioners to prevent vascular obstruction using existing medical therapies like beta adrenergic blocking agents.

4 Claims, 17 Drawing Sheets

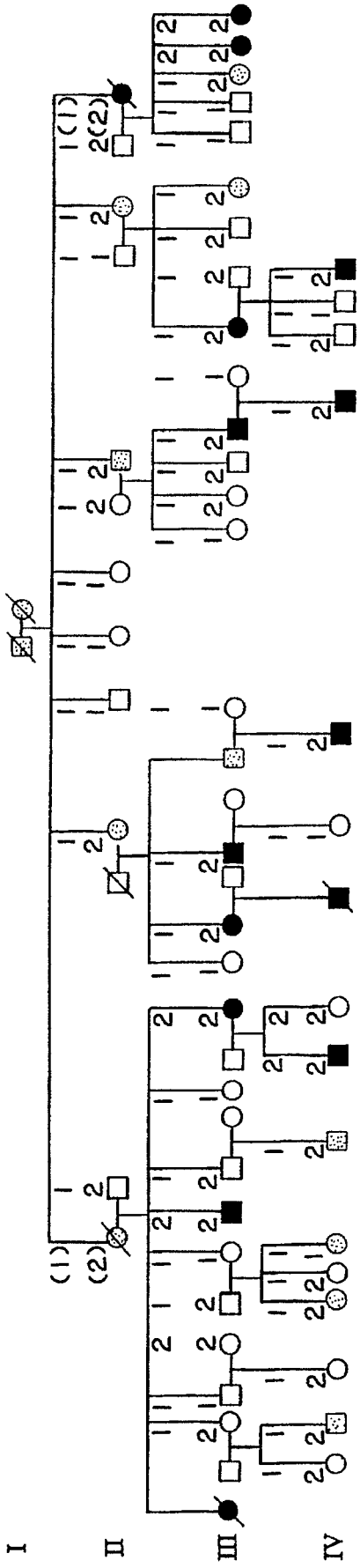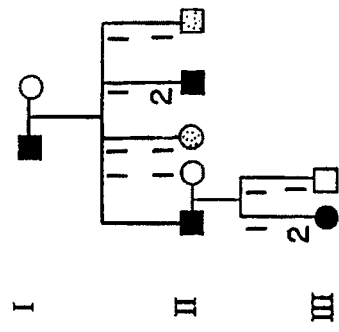
FIG. IA
FIG. IB

K1861 FIG. IC
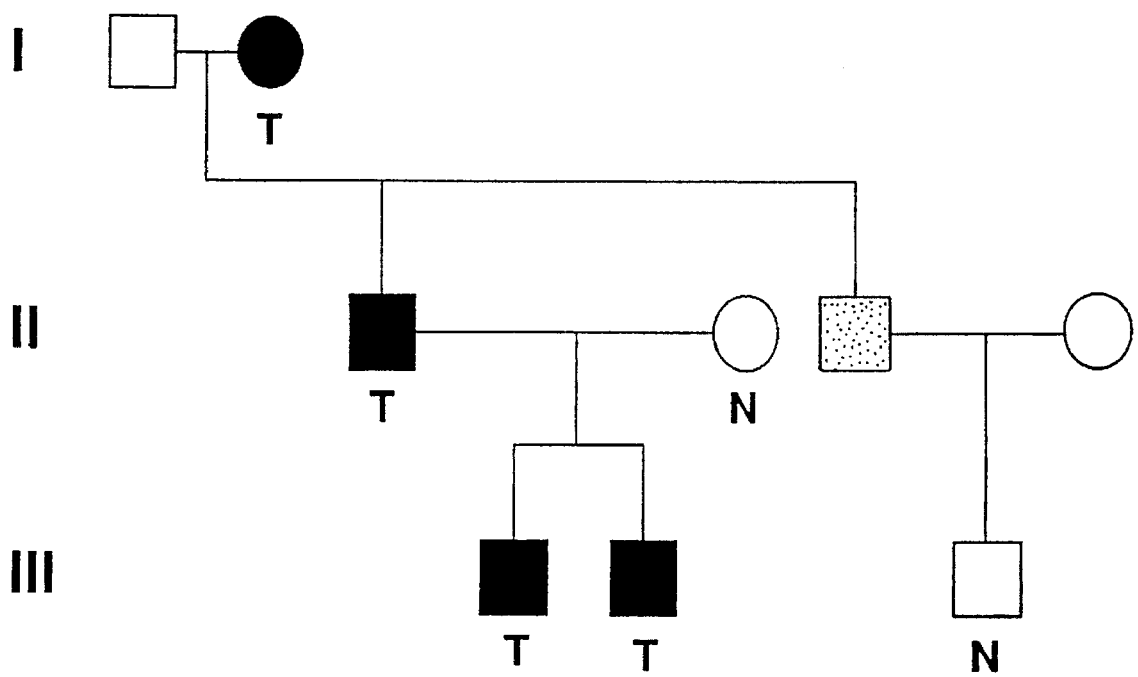
K2049 FIG. ID
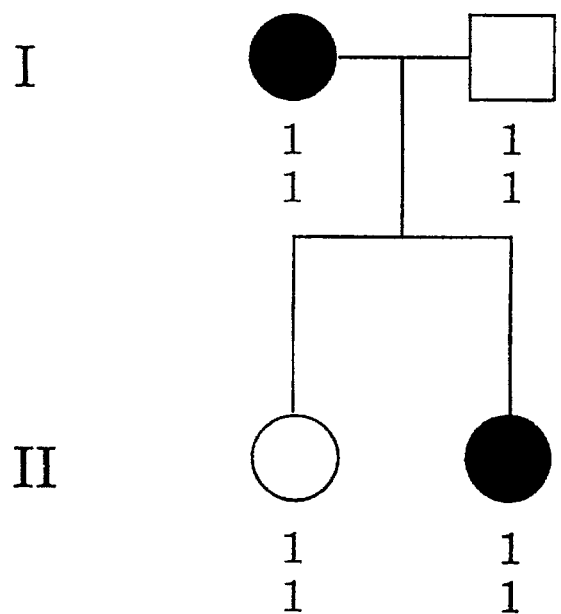

Probe: Elastin cDNA

Probe: N-2.8

```
T1  CTCATCTGCAAAATGGAATGACAATAGTGCCTACCTTTCCTGCTGCA
N   ----------------------------------------------

T1  GCTGTAGATACTATTACCGTTGTTTGTTTGTTTGTTTGTTTGTTTTGA
N   ----------------------------------------------

T1  CCTGCAGCCTCCATCTCCCGGGTTCAAGTGATTCTCCTGCCTCAGCCT
N   ----------------------------------------------

T1  TTTTTCGTAGAAACAGGGTTTCACCGTGTTGGCCAGGCTGGTCTCAAA
N   ----------------------------------------------

T1  CAGGTGTGAGCCACGCACCCGGCTTACAAAAGAACTTTTAAGGCCAGG
N   ----------------------------------------------

T1  GAGTTGGAGGCTGCAGTGAACTATGATTGTACCACTGCACTCCAGCCG
N   ----------------------------------------------

T1  TCCTGTCCACTGCTCCTCCACAGTGTCACATGGCCCCTGCCACCTGTC
N   ----------------------------------------------
                                    Breakpoint ↓      Stop
T1  CTCATTTTCCCTCCTCTCCCCGCAGGAGCAGCAGTGCTGAAATGACAC
N   ------------------------------------------CTGGGGTCCTT T1  TTGGCGTTCAGTGTAAAGTGTATCGGAGTGCGGAAAATGCGCAGGGCA
N   AGTTGAAACCCAGGAGGGGCAGGGTGGGGAGGGAATCTAACCAGTACA T1  AACAAGGAAAACCGGCCTGACTGGGGGGTGAATTCAGCAGGGAGTAAA
N   CGCTGCCGCAGCCAAAGCTGCTGCCAAAGCCGCCCAGTTTGGTGAGCA T1  GCATTGCCTGGCTCTCTCCGCGGCGGGCTAAGTTAACCGCGGGTCCAG
N   AGCTTCTGACCAGGCACTGTAGACTCAGAGTCCCTGCCCCAGACACCT T1  TCGGGAGCCGCCGCTGCTAGTGAGAGCCGGGGCACACGCTCCTCCCCG
N   GTCCCCAGAGGACACCTCCGCCCTCCACAGGCCGAGGCTTCAGTCCCA T1  CCTAGGCGACCCAGGACACAGCCCGCGCGCAGCCCACCCGCCCGCCGC
N   AGCCGCTGGGCTCGGAGGACTCGGAGTCGGAGGGCTTGGAGTTCCAGG
```

FIG. 6A

ATGCATAAAAAATGGGCTGCTAAGTGTGAAGCACTCAAAATGTTAAGTGCCT

CAGAGTCTTGCTCTGTCGCCCAGGCTGGAATGCAGTGGTACGATCTTGGCTC

TCCAAGTAGCTGGGATTACAGCGCCCGCCACCACGCCTGGCTAATTTTTGTA

CTCCTGACCTCAGGTGATCCACTAGCCTCAGCCTCCCAAAGTGCTGGGATTA

CACAGTGGTTCACACTTCGGGAGGCTAAGGCAGGAGGATCGCATGAGCCCAG

GGGTGACAGAGCAAAACCCCATCTCAAAATGAAACAAAATATGGACTGGACT

TGCTTGCCTTGTGTCCCTGGGGCAGGGAGACCCATCGTTCAGAAATGGAACA

CAGCACAGTGGCAGGCCTTCCAATCTGGAGCACGGTCCACACAACTTCCGAA
GGAGGGCTCGGGGCTCTCGGTGGAGTAGGCATCCCAGGCGGTGTGGTGGGTG

Elastin Exon 28

TTGCCAACTATAGATGCTCGGAGTAATTCAGTGTATTCAGAGAACACGGTGA
GAGTGCCTCCCTGAACTCGGTCTGTGTTCCCAGGAGCCGGACCCGCCGCCGC

TCTGATCGGCATCAGGTCTGCGGAAAGGAGCTGGTGAGCACGACACCACCAC
CTGGGTGGAGGTGGGAGCTGCCGCCAGCCCCAGGCCCCAGGGTGTGGGAGG

GTGCGGGCCATGGTCTTGGGGAGGGTGCTGGGTGCGCTCGAGCAGGCTAGCG
CCTGGCTCCACTGTGCCATCGAAGGCCAGGGGAGACCTCAGGCTCCACCTGT

GTACCTCCTCCAGCATCACCAGGGGAGGAGAGGGTCGGGGCCACAAGGGCCG
CCTTTCTGACCAGCGGAGTCTAATGCTCAGCTGTCTCCACAGGCCTAGTGGG

CTGCCAGAGCTGCTCGGCCCGCAGCCAGGGGACAGCGGCTGGTCGGAGGCT
TGTTGGGGGCCTTGGAGGTGAGAGTTGTTCTGAAATCAGTGAGTGTGTGTGG

FIG. 6B

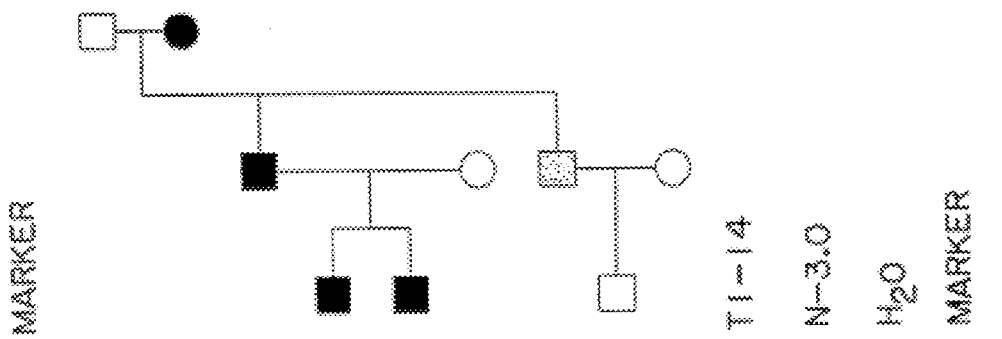
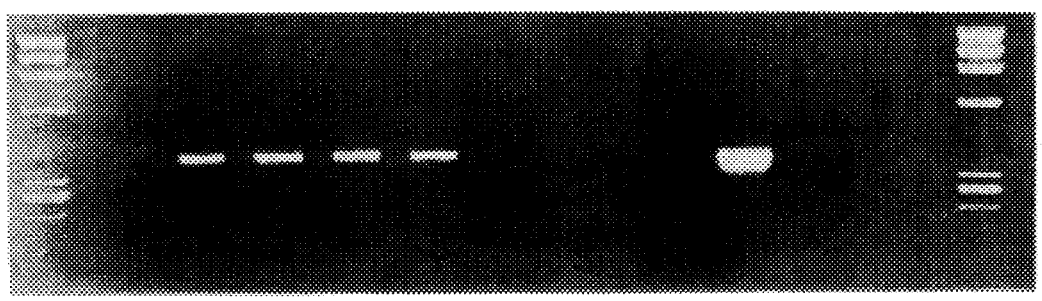
Primers:   TBF + TBR
FIG. 7B
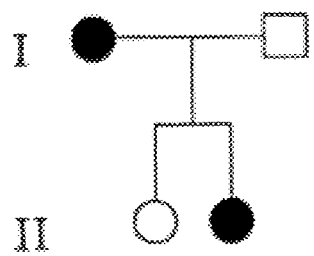
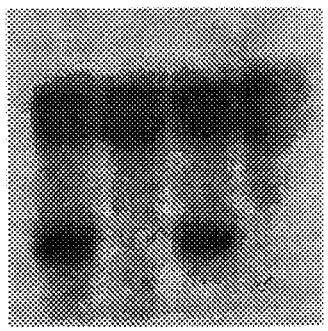
—12.5 kb
—11.5 kb
—8.5 kb
PROBE: 5-9
FIG. 8

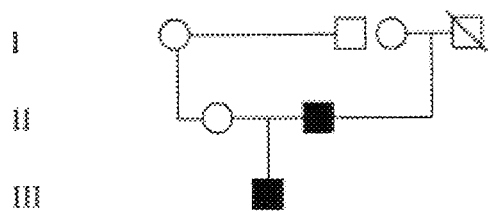
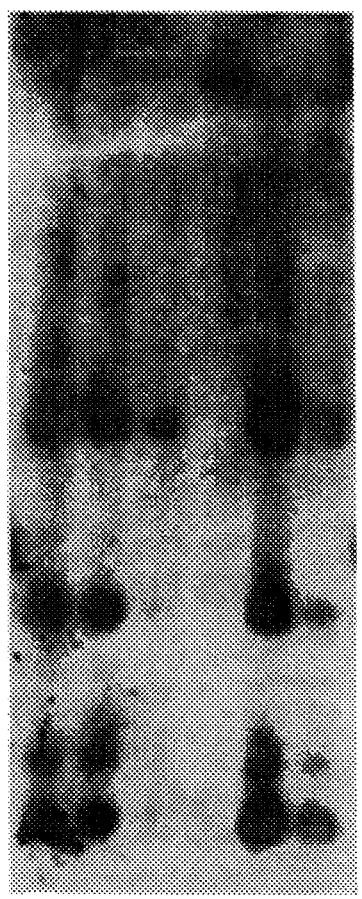
Probe 5-4
FIG. 10

K1806
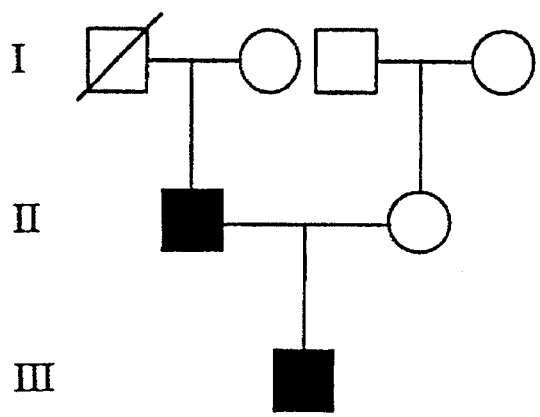
FIG. IIA
K2042
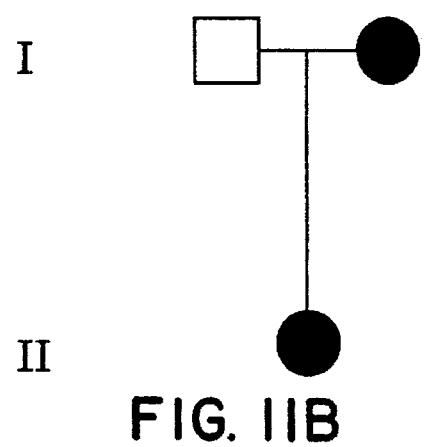
FIG. IIB
K1998
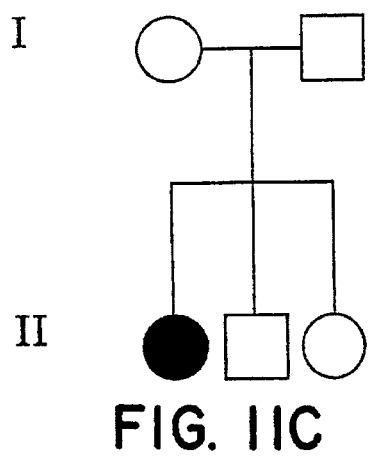
FIG. IIC
K2016
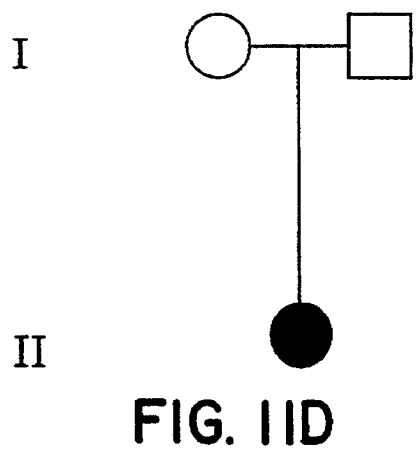
FIG. IID

K2767

K1866

K1868

K1888

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:1:

CGCTCTAGAC AAGGCCTGGG GGAAATTTAC ATCC  34

( 2 ) INFORMATION FOR SEQ ID NO:2:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:2:

CGCAAGCTTC TGGAGGCCTG GGAGCCAGTT TG  32

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:3:

GGAGAGAGCC AGGCAATGC  19

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:4:

AAAATGCGCA GGGCATTGCC AA  22

( 2 ) INFORMATION FOR SEQ ID NO:5:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:5:

CCTGGACTTG GAGTTGGTGC TGG    23

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:6:

CCGAGCCCTC CAAGGACC    18

( 2 ) INFORMATION FOR SEQ ID NO:7:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:7:

ATCGTTCAGA AATGGAACAC TCA    23

( 2 ) INFORMATION FOR SEQ ID NO:8:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:

(A) ORGANISM: Homo sapiens (xi) SEQUENCE DESCRIPTION: SEQ ID NO:8:

ACCTGGACCC GCGGTTAACT TA 22

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:9:

AGATGGCGGG TCTGACGG 18

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:10:

TCCCAGGAGC TCGGTTCCCC G 21

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:11:

CACCTGGGAT CCCACGAGGT G 21

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
    (A) ORGANISM: Homo sapiens (x i) SEQUENCE DESCRIPTION: SEQ ID NO:12:

GGCCACAAGC TTTCCCCAGG CA      22

DIAGNOSIS OF WILLIAMS SYNDROME

This application is a continuation of application Ser. No. 08/041,576, filed 5 Apr. 1993, abandoned.

This application was made with Government support under Grant No. RO1HL4807, funded by the National Institutes of Health, Bethesda, Md. The United States Government has certain rights in the invention.

BACKGROUND OF THE INVENTION

The present invention is directed to a process for the diagnosis and prevention of supravalvular aortic stenosis (SVAS) and Williams syndrome. SVAS and Williams syndrome is diagnosed in accordance with the present invention by analyzing the DNA sequence of the elastin gene of an individual to be tested and comparing the DNA sequence to the known DNA sequence of a normal elastin gene. Alternatively, the elastin gene of an individual to be tested can be screened for mutations associated with SVAS or Williams syndrome. Prediction of SVAS and Williams syndrome will enable practitioners to prevent these disdorders using existing medical therapy.

The publications and other materials used herein to illuminate the background of the invention or provide additional details respecting the practice, are incorporated by reference and for convenience are respectively grouped in the appended List of References.

Supravalvular aortic stenosis (SVAS) is an inherited vascular disorder (1). As its name implies, narrowing of the ascending aorta is a dominant feature of this disease, but other arteries, including the pulmonary arteries, may be affected. If uncorrected, SVAS may lead to increased intracardiac pressure, myocardial hypertrophy, heart failure and death. The incidence of SVAS is estimated to be 1 in 25,000 live births. The vascular abnormalities typical of SVAS can be inherited as an isolated, autosomal dominant trait (1–3) or as part of a second disease, Williams syndrome, a developmental disorder that affects multiple organ systems (2–4). In addition to vascular disease, manifestations of Williams syndrome include hypertension, mental retardation, an unusually gregarious personality, premature greying of the hair, premature aging of the skin, joint laxity early in life followed by joint contractures, dysmorphic facial features and infantile hypercalcemia (4). The relationship between SVAS and Williams syndrome was previously undefined. Occasionally patients with Williams syndrome have been noted in families with SVAS.

SVAS was first described in 1842 (5), but the pathogenesis of this disorder was unknown until now. Mechanistic hypotheses have been based on clinical and pathological studies, but these data are conflicting. It is not clear, for example, whether hypertrophy or hyperplasia of medial smooth muscle is the more prominent feature of this disorder. O'Conner et al. (6) examined tissue from six individuals with SVAS; two of these cases were familial, one was a sporadic case of SVAS, and three had Williams syndrome with SVAS. These investigators did not discover any significant pathologic differences between the individuals with different SVAS inheritance patterns. They noted that the medial layer of the aorta in all patients showed a haphazard arrangement of thick elastic fibers, excessive collagen, hypertrophied smooth-muscle cells, and scant ground substance. This contrasts with normal medial tissue, which is highly organized and arranged in parallel layers of connective tissue and smooth muscle. They also observed that smooth muscle cells formed clumps or bundles and were the major component of the medial layer. In a study of a single individual with SVAS, Perou also showed that the diseased media contained excessive smooth muscle (7). The resulting pattern was that of irregular fascicles of smooth muscle surrounded by fibrous and collagenous tissue. In contrast to these studies, Pober et al. recently reported a study of seven individuals with SVAS and Williams syndrome, noting that the medial layer of affected aortas contained an increased number of smooth muscle cells and normal to decreased collagen. These investigators also observed an elevated level of platelet-derived growth factor (PDGF) and concluded that increased quantities of PDGF stimulate smooth muscle proliferation and cause the cardiovascular abnormalities of SVAS (8).

The pathogenic mechanisms underlying Williams syndrome are unknown, but many hypotheses have invoked a mechanism of abnormal calcium metabolism (9). These hypotheses are based on the intermittent observation of infantile hypercalcemia in Williams syndrome as well as studies showing that excessive vitamin D administration can produce pathologic changes in the supravalvular aortic wall of rabbits during development (10). Recent attempts to repeat this work, however, have failed and the hypothesis involving vitamin D has been questioned (11). Researchers have tried to identify a causal relationship between calcitonin-gene-related peptide (CGRP) and Williams syndrome. Hitman et al. investigated 13 families with Williams syndrome and infantile hypercalcemia for germ line mutations in the CGRP gene, and found no mutations (12). Using linkage analysis, investigators have also excluded the CGRP gene, which is located on chromosome 11, in a family with autosomal dominant SVAS (13).

Diagnosis of SVAS has been based on family history, physical examination and echocardiography. Unfortunately, these tests may be ambiguous, making early detection of this disorder difficult. The recent advent of high quality two-dimensional and color flow Doppler echocardiography have improved non-invasive screening for SVAS (14), but invasive tests such as cardiac catheterization and angiography are more sensitive. Currently, vascular surgery is the only treatment option for SVAS. Therefore, it is an object of the present invention to provide better diagnostic methods for screening for SVAS and Williams syndrome which will ultimately lead to new medical therapies for their prevention.

SUMMARY OF THE INVENTION

The present invention demonstrates the molecular basis of SVAS and Williams syndrome. More specifically, the present invention has determined that molecular variants of the elastin gene cause or are involved in the pathogenesis of SVAS and Williams syndrome. Analysis of the elastin gene will provide an early diagnosis of subjects with SVAS and Williams syndrome. The diagnostic method comprises analyzing the DNA sequence of the elastin gene of an individual to be tested and comparing it with the DNA sequence of the native, non-variant elastin gene. In a second embodiment, the elastin gene of an individual to be tested is screened for mutations associated with SVAS or Williams syndrome. The ability to predict SVAS will enable physicians to prevent the disease with medical therapy like beta blocking agents. Finally, this invention has implications for the cause and treatment of common vascular disease, like atherosclerosis.

BRIEF DESCRIPTION OF THE FIGURES

FIG. 1 shows the pedigree structure and elastin genotypes for SVAS families K1773 (FIG. 1A), K1779 (FIG. 1B), K1861 (FIG. 1C) and K2049 (FIG. 1D). Affected individuals having the characteristic pattern of elevated Doppler velocity and narrowing of the ascending aorta or pulmonary arteries on echocardiograms are represented by filled circles (females) and squares (males). Unaffected individuals are represented by open squares or circles. Family members who had an equivocal phenotype or for whom no phenotypic data were available are represented by stippled squares and circles. Above each symbol, individual alleles are listed for the elastin polymorphic PCR marker (15). At this marker locus the restriction enzyme BstNI revealed two distinct alleles within the families. The disease gene cosegregates with the 244-bp allele (allele 2) in families K1773 and K1779. Alleles shown in parentheses were inferred. Individuals carrying a translocation are indicated by T and those not carrying the translocation are indicated by N in family K1861.

FIG. 4A show an ideogram of chromosome 7 showing location of the elastin locus with the intron and exon structure, and probes used to define the translocation. Numbering of exons was first described for the bovine elastin gene; the human elastin gene lacks exons 34–35 (39). FIG. 4B shows that hybridization of an elastin subclone (N-2.0) proximal of the translocation breakpoint detects a 450 kb anomalous Not I fragment in DNA from SVAS patients including the individual with features of Williams syndrome. By contrast, a subclone (N-2.8) distal of the breakpoint detects a 1000 kb anomalous Not I fragment in DNA from affected members of kindred 1861. Both probes detect the normal 700 kb Not I fragment which is also seen in unaffected family members. These data prove that the SVAS-associated translocation disrupts the elastin gene.

FIG. 5A shows restriction map of N, the non-translocated elastin allele (chromosome 7) cloned from SVAS patient III-1. Elastin exons are indicated by filled bars and numbered. Restriction enzymes (B, Bam HI; H, Hind III; E, Eco RI; K, Kpn I; P, Pst I; S, Sma I) are indicated. Expanded restriction map for a 3.0 kb subclone (N-3.0) is shown below. FIG. 5B shows a restriction map of T1, a genomic clone from SVAS-patient III-1 containing a translocation breakpoint. The site of the breakpoint region is indicated. Chromosome 7 sequences containing elastin exons are at left. Translocated sequences from chromosome 6 are at right. Expanded restriction map for 2.2 kb of T1-14 (a subclone of T1) is shown below.

FIG. 6 shows nucleotide sequence of the T1 translocation breakpoint. Nucleotide sequence of the T1 (translocation allele, top) and N (nontranslocated elastin allele, bottom) showing complete identity until the translocation breakpoint indicated by an arrow. Nucleotide identity is indicated as a dash. This rearrangement disrupts elastin exon 28, resulting in a new stop codon (TGA) as indicated by a small box. Sequences encoding elastin exon 28 in the normal clone are underlined. Alu sequences within intron 27 of the normal elastin clone were identified near the translocation breakpoint and are enclosed in a large box.

FIGS. 7A–7B show PCR analyses indicating that T1represents a translocation breakpoint. FIG. 7A shows a map of the T1 clone showing the translocation breakpoint and the location of oligonucleotide primers. FIG. 7B shows that olignucleotides primers directed across the translocation breakpoint (TBF and TBR) yield a PCR product of the predicted size (370 bp) in affected family members of kindred 1861 and in a subclone of T1 (T1-14), but not in unaffected family members or in a normal elastin subclone (N-3.0).

FIG. 8 shows that hybridization of elastin probe to Bcl I digests revealed 8.5 kb abberent fragments in DNA from affected members of K2049. The 12.5 and 11.5 kb fragments were observed in affected and unaffected members of this kindred. These data indicated that 3' elastin sequences are deleted in affected members of this SVAS family.

FIG. 10 shows hybridization of an elastin genomic probe to Pst I digests of DNA from Williams syndrome patient II-2 which reveals a restriction fragment of 3.5 kb but does not show the common 2.0 and 1.6 kb fragments. Williams syndrome patient III-1 did not inherit the 3.5 kb Pst I fragment from his father; he only inherited the 2.0 and 1.6 kb fragments from his mother. These data show that affected father and son both carry null mutations of the elastin gene. Identical results have been found in a second family with Williams syndrome.

DETAILED DESCRIPTION OF THE INVENTION

Figure 2:
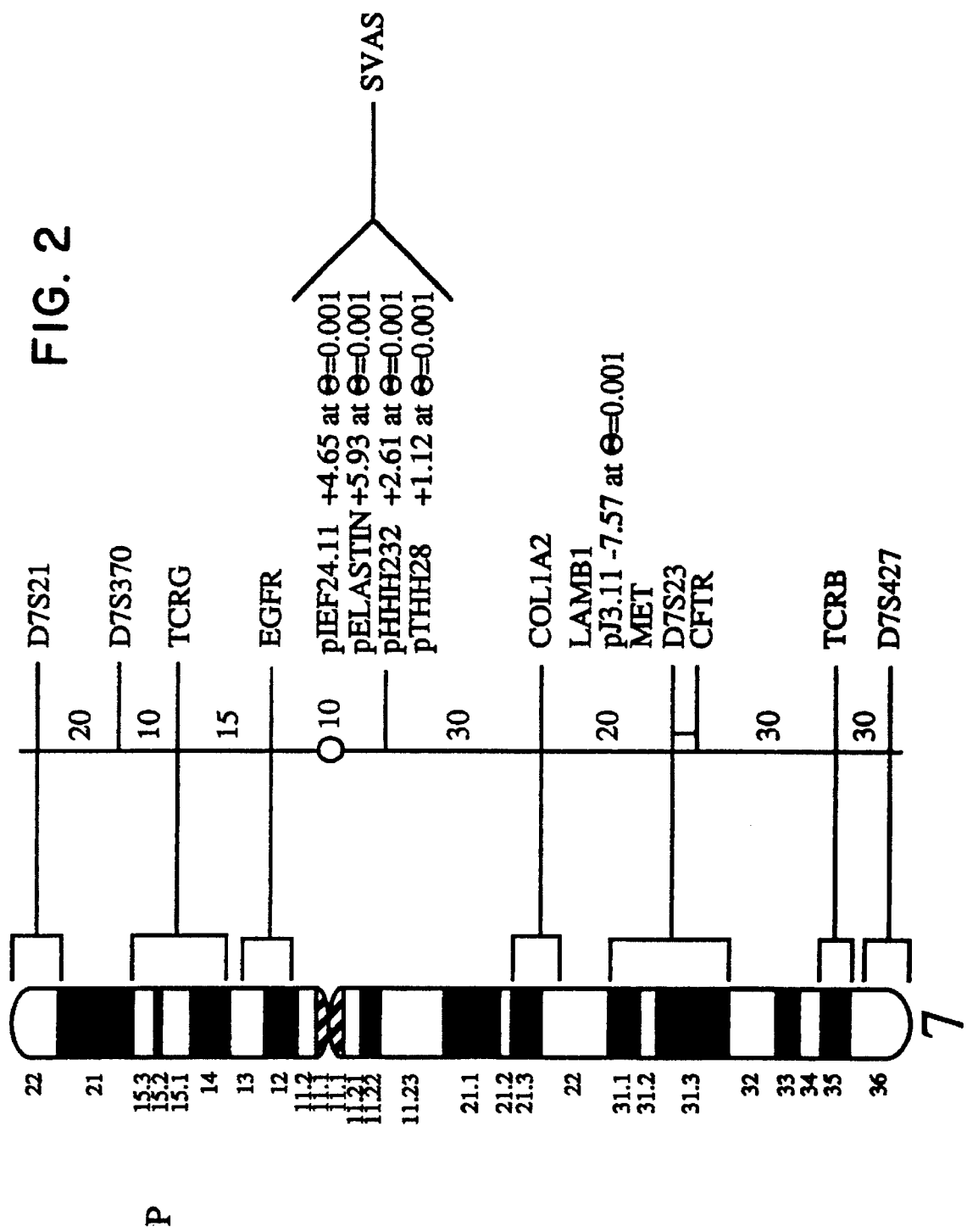
FIG. 2 shows the approximate map location of the SVAS disease gene. Genes and polymorphic loci mapped to chromosome 7 are shown at right. The approximate genetic distance between these loci in cM is shown on the diagram at center (16). The approximate subsegmental location of these loci is shown on the idiogram at left. In K1773 and K1779, SVAS is linked to pHHH232, pIEF24.11, pTHH28 and elastin, which are mapped approximately to 7q11 between the centromere and COL1A2 (collagen). Pairwise lod scores between a DNA marker and the disease phenotype are indicated.

The present invention is directed to the determination that SVAS and Williams syndrome map to the elastin gene and that molecular variants of the elastin gene cause or are involved in the pathogenesis of SVAS and Williams syndrome. The present invention is further directed to methods of screening humans for the presence of elastin gene variants associated with SVAS or Williams syndrome. Since SVAS or Williams syndrome can now be detected earlier (i.e., before symptoms appear) and more definitively, better treatment options will be available in those individuals identified as having SVAS or Williams syndrome. Finally, the present invention has implications for the cause and treatment of common vascular disease, such as atheroselerosis.

Supravalvular aortic stenosis (SVAS) is an inherited disorder that causes hemodynamically significant narrowing of the ascending aorta and other arteries. SVAS can be inherited as an isolated trait or as part of the Williams syndrome, a developmental disorder that also results in hypertension, mental retardation, a personality disorder and premature aging of the skin.

Two approaches have been utilized herein to identify the elastin gene as the cause of SVAS and Williams syndrome, namely linkage analysis and the identification and characterization of disease-associated gene abnormalities. In linkage analysis, one attempts to identify co-inheritance of a phenotype (e.g., SVAS) and a genotype (DNA polymorphism). Disease-associated gene abnormalities include chromosomal rearrangements, gross and microscopic deletions or additions, and sequence differences. These two approaches led to the identification of the elastin gene as the cause of SVAS and Williams syndrome.

SVAS was completely linked to the elastin locus on chromosome 7q11 by phenotypic and linkage analyses (details provided in the Examples) by studying two multigenerational families with SVAS. Kindred 1773 is a Kentucky family of Irish decent and consists of 47 family members who are at risk for SVAS (FIG. 1A). The second family, K1779, is of German decent and contains 9 family members (FIG. 1B) including spouses, most of whom live in Indiana. The clinical features of these families are similar and typical of familial SVAS. In both families, several affected members required surgical correction of SVAS, and in one family (K1773), three family members died of this disorder. The linkage analysis was performed using highly polymorphic DNA markers spanning the genome. Proof that the elastin gene causes or is involved in the pathogenesis of SVAS was performed by characterizing the disease-associated gene abnormality of a 6p21/7q11 translocation in a SVAS family. The 6p21/7q11 translocation cosegregates with the SVAS phenotype in the unique family K1861 (FIG. 1C). It was found that this translocation disrupts the elastin gene. In a second SVAS family, K2049, a deletion of the 3' end of the elastin gene was identified. Thus, molecular variants of the elastin gene have been found to cause or be involved in the pathogenesis of SVAS.

Proof that the elastin gene causes or is involved in the pathogenesis of Williams syndrome was accomplished by analyzing the disease-associated gene abnormality in two familial and six sporadic cases of Williams syndrome. It was found that hemizygosity at the elastin locus, i.e., one allele of the elastin gene was absent, causes or is involved in the pathogenesis of Williams syndrome.

The identification of the association between elastin gene mutations, SVAS and Williams syndrome permits the early presymptomatic screening of individuals to identify those at risk for developing SVAS or Williams syndrome. To identify such individuals, the elastin alleles are screened for mutations. The elastin alleles are screened for mutations either directly or after cloning the alleles. The alleles are tested for the presence of nucleic acid sequence differences from the normal allele using any suitable technique, including but not limited to, one of the following methods: fluorescent in situ hybridization (FISH), direct DNA sequencing, PFGE analysis, Southern blot analysis, SSCP analysis, linkage analysis, RNase protection assay and allele specific oligonucleotide (ASO) dot blot analysis. For example, either (1) the nucleotide sequence of both the cloned alleles and normal elastin gene or appropriate fragment (coding sequence or genomic sequence) are determined and then compared, or (2) the RNA transcriptions of the elastin gene or gene fragment are hybridized to single stranded whole genomic DNA from an individual to be tested, and the resulting heteroduplex is treated with Ribonuclease A (RNase A) and run on a denaturing gel to detect the location of any mismatches. Two of these methods can be carried out according to the following procedures.

The alleles of the elastin gene in an individual to be tested are cloned using conventional techniques. For example, a blood sample is obtained from the individual. The genomic DNA isolated from the cells in this sample is partially digested to an average fragment size of approximately 20 kb. Fragments in the range from 18–21 kb are isolated. The resulting fragments are ligated into an appropriate vector. The sequences of the clones are then determined and compared to the normal elastin gene.

Alternatively, polymerase chain reactions (PCRs) are performed with primer pairs for the 5' region or the exons of the elastin gene. PCRs can also be performed with primer pairs based on any sequence of the normal elastin gene. For example, primer pairs for one of the introns can be prepared and utilized. Finally, PCR can also be performed on the mRNA. The amplified products are then analyzed by single stranded conformation polymorphisms (SSCP) using conventional techniques to identify any differences and these are then sequenced and compared to the normal elastin gene sequence.

Individuals can be quickly screened for common elastin gene variants by amplifying the individual's DNA using suitable primer pairs and analyzing the amplified product, e.g., by dot-blot hybridization using allele-specific oligonucleotide probes.

The second method employs RNase A to assist in the detection of differences between the normal elastin gene and defective genes. This comparison is performed in steps using small (~500 bp) restriction fragments of the elastin gene as the probe. First, the elastin gene is digested with a restriction enzyme(s) that cuts the elastin gene sequence into fragments of approximately 500 bp. These fragments are separated on an electrophoresis gel, purified from the gel and cloned individually, in both orientations, into an SP6 vector (e.g., pSP64 or pSP65). The SP6-based plasmids containing inserts of the elastin gene fragments are transcribed in vitro using the SP6 transcription system, well known in the art, in the presence of [α-$^{32}$P]GTP, generating radiolabeled RNA transcripts of both strands of the elastin gene.

Individually, these RNA transcripts are used to form heteroduplexes with the allelic DNA using conventional techniques. Mismatches that occur in the RNA:DNA heteroduplex, owing to sequence differences between the elastin fragment and the elastin allele subclone from the individual, result in cleavage in the RNA strand when treated with RNase A. Such mismatches can be the result of point mutations or small deletions in the individual's elastin allele. Cleavage of the RNA strand yields two or more small RNA fragments, which run faster on the denaturing gel than the RNA probe itself.

Any differences which are found, will identify an individual as having a molecular variant of the elastin gene and the consequent presence of SVAS, Williams syndrome or predisposition to common vascular disease.

Genetic testing will enable practitioners to identify individuals at risk for SVAS and Williams syndrome at, or even before, birth. Presymptomatic diagnosis of SVAS and Williams syndrome will enable prevention of these disorders. Existing medical therapies, including beta adrenergic blocking agents, will prevent and delay the onset of severe vascular disease in SVAS and Williams syndrome (currently the only therapy for these disorders is open-chest surgery). Finally, this invention changes our understanding of the cause and treatment of common vascular disease like atherosclerosis, a disease that kills hundreds of thoussands of individuals. Existing art has focused on cholesterol and high blood pressure in the cause and treatment of vascular disease. This invention demonstrates that inelasticity of blood vessels can cause vascular obstruction. This finding will lead to a new avenue for medical therapy of vascular disease. Therefore, individuals with molecular variants in the elastin gene may be predisposed to common vascular disease.

The present invention is further detailed in the following Examples, which are offered by way of illustration and are not intended to limit the invention in any manner. Standard techniques well known in the art or the techniques specifically described below are utilized.

EXAMPLE 1

Methods for Phenotypic Evaluation

Two multigenerational families with SVAS (FIGS. 1A and 1B) were studied. Kindred 1773 was of Irish descent and Kindred 1779 was of German descent. Informed consent was obtained from all study participants or their guardians, in accordance with standards established by local institutional review boards. To determine if family members and spouses had signs of SVAS or Williams syndrome, physical examinations were performed. The method of identification of SVAS was similar to that described previously (14). Echocardiograms were performed with the use of Hewlett-Packard Sonos 500 and VingMed CFM 700 machines with 2.5 to 5.0 MHz duplex imaging and Doppler probes as determined by patient size. A 2.5 MHz continuous-wave offset imaging pencil probe was used for suprasternal continuous-wave Doppler sampling. Color flow Doppler was used in all of the patients to assess blood flow acceleration in the aortic root and pulmonary arteries. Each examination was recorded on 0.5 in. (1.27 cm) VHS videotape.

Standard parasternal long axis, short axis, apical four chamber, subcostal and suprasternal views were recorded in all patients when technically feasible. In addition, the proximal ascending aorta was imaged in the long axis from high left or right parasternal views. Two-dimensional echocardiographic measurements of the left ventricular outflow tract, aortic annulus, aortic root at the sinus of Valsalva, ascending aorta at the sinotubular junction (or its narrowest point), descending aorta below the origin of the left subclavian artery, main pulmonary artery, and the narrowest portions of the proximal right and left pulmonary arteries were determined for each patient when technically feasible. Peak blood flow velocities were measured by Doppler from the ascending aorta at the apex and suprasternal notch (continuous wave), main pulmonary artery (pulsed wave), right pulmonary artery (pulsed or continuous wave), and left pulmonary artery (pulsed or continuous wave). The velocity time integral and ejection time were recorded from the ascending aorta, left ventricular outflow tract and pulmonary artery. Peak aortic and pulmonary artery flow velocities were compared with the normal range of values (aortic: adult 1.0–1.7 m/s, children 1.2–1.8 m/s; pulmonary: adult 0.6–0.9 m/s, children 0.7–1.1 m/s; ref. 19). M-mode measurements were recorded from the left and right ventricular cavities, septum, posterior wall of the left ventricle, aorta, aortic valve opening, and left atrium (14).

To determine the phenotype of individuals, all Doppler echocardiographic data were independently reviewed without knowledge of genotypic data. Individuals were classified as affected, uncertain, and unaffected based on catheterization, angiography and surgical findings. If catheterization data were unavailable, phenotype was determined based on echocardiographic impression of narrowing of the aorta at the sinotubular junction and the supravalvular pulmonary region, increased Doppler blood flow velocity in the ascending aorta, increased flow velocity in the main pulmonary artery, and/or increased blood flow velocity in the peripheral pulmonary arteries. Family members were scored on a scale from –6 (no evidence of SVAS) to +6 (strong evidence of SVAS). For linkage analysis, individuals with impression scores of –2 and lower were classified as unaffected, +2 and greater as affected, and –1, 0 and +1 as uncertain. Phenotypic criteria were identical for females and males.

EXAMPLE 2

Methods for DNA Analysis

Approximately 40 mls of blood were obtained from each family member for genetic analyses. Human genomic DNA was purified from leukocytes and from Epstein-Barr virus-transformed cell lines (20, 21). Five mg of DNA from each individual was digested with restriction endonucleases (Molecular Biology Resources, Milwaukee, Wis.) overnight under conditions recommended by the manufacturer. Digestion reactions included 4 mM spermidine. DNA fragments were separated by agarose gel electrophoresis, soaked in 0.4N NaOH for 30 min and transferred overnight (22) to nylon membranes (Hybond N+, Amersham, Inc.). After transfer, filters were washed once in 0.5M Tris (pH 7.5) and once in 0.1×SSC/0.1% SDS before hybridization. Prehybridization of membranes was carried out in a hybridization solution containing 10% polyethylene glycol, 7% SDS, 1.5×SSPE and 250 mg/ml human placental DNA at 65° C. for 24 hours. Plasmids were denatured and labeled with [$^{32}$P]dCTP (New England Nuclear) by random primer synthesis (23) to high specific activity (typically 1–5×10$^9$ cpm/mg DNA). Radiolabeled probe DNAs were hybridized overnight to the human genomic DNA transfers at 65° C. in fresh hybridization solution. After hybridization, membranes were washed twice for 15 min. each at room temperature in 0.1×SSC and 0.1% SDS and then washed for 30 min. at 65° C. Membranes were exposed to X-ray films backed by intensifying screens at −70° C. overnight. Included in the 140 polymorphic probes used were: pTHH28 (24), pIEF24.11 (25), pHHH232 (26), pJ3.11 (26).

Polymorphic genomic sequences at the elastin locus (15) were amplified by polymerase chain reaction (PCR) with a final volume of 25 ml containing 200 ng genomic DNA template. Reactions contained 0.4 mM of each unlabeled oligonucleotide primers:

HEIG15: 5'-CGCTCTAGACAAGGCCTGGGGGAAAT TTACATCC-3' (SEQ. ID NO:1) and

HEIG16: 5'-CGCAAGCTTCTGGAGGCCTGGGAGCC AGTTTG-3' (SEQ. ID NO:2) (15).

The reactions further contained 200 mM each of dNTPs (Pharmacia), 1×PCR buffer (10 mM Tris pH 8.3, 50 mM KCl, 1.5 mM MgCl), and 1.25 U Taq DNA polymerase (Perkin-Elmer-Cetus). Samples were overlaid with mineral oil and processed through 30 PCR cycles: 1.5 min. at 94° C., 1 min. at 65° C., 1 min. at 72° degrees C and a final extension step of 7 min. at 72° C. Amplified products were incubated with BstNI according to the manufacturer's recommendations. Digestion products were run for 3 hours on a 4%:0.5% Nusieve/LE agarose gel and stained with ethidium bromide.

EXAMPLE 3

Methods for Linkage Analysis

Polymorphic patterns were determined for each individual without knowledge of phenotype. Genotypic data were entered into a computer relational data base, and the output listings were checked against the autoradiograms to avoid clerical errors. Linkage analyses were performed using the programs MLINK and LINKMAP of the LINKAGE package (27). Lod scores were calculated at various recombination fractions for each probe. Based on results from segregation analysis, an autosomal dominant inheritance of a single gene with a penetrance of approximately 0.90 was assumed. Allele frequencies for markers were from previous calculations (15, 24–27). Male and female recombination fractions were assumed to be equal.

EXAMPLE 4

Analysis of Phenotypic Evaluation

Kindred 1773 was of Irish descent and included 47 family members at risk for SVAS. The second family, Kindred 1779, was of German descent and had seven family members at risk for this disorder. Seven affected members of these kindreds required surgical correction of SVAS, and at least three died of this disorder; two individuals died in early childhood (18 months and 3 years) during catheterization and surgery, respectively, and one died at age 39 of heart failure after refusing surgery. There was no evidence that these families were related. The clinical features of affected family members, including variability of cardiac expression, were typical of familial SVAS with one exception. In addition to severe SVAS, one affected member of Kindred 1779 (III-1) had learning disability (IQ of 76), gregarious personality, hoarse voice, joint contractures, and mild dysmorphic facial features. These characteristics satisfied the arbitrary diagnostic index for Williams syndrome (28).

Segregation analyses indicated an autosomal dominant pattern of SVAS gene inheritance with incomplete penetrance. This analysis suggested that some SVAS gene carriers appeared unaffected by the disease. To avoid misclassifying individuals, a conservative approach to phenotypic assignment was taken. Each individual was given an impression score based on the extent of observed SVAS, supravalvular pulmonic stenosis or peripheral pulmonary artery stenosis. Impression scores, coupled with catheterization, angiographic and surgical data, were used to classify family members as affected, unaffected, or uncertain. Forty-seven individuals from K1773 and 7 individuals from K1779 were examined, and the results are shown in Table 1. As a result, 17 family members were classified as affected, 23 as unaffected and 14 as uncertain. As history and physical examination for spouses were normal in all but one instance, it was assumed that spouses were not affected by this rare disorder; one spouse had a click-murmur, and echocardiogram confirmed mitral valve prolapse.

TABLE 1

Phenotype Evaluations of SVAS Families

| Individual | Age | Ao Flow m/s | Po Flow m/s | Sinotubular Junction (cm.) | Impression Score | Cardiac Cath | Affected Status |
|---|---|---|---|---|---|---|---|
| K1773 | | | | | | | |
| I-1 | deceased | — | — | — | — | — | U |
| I-2 | deceased | — | — | — | — | — | U |
| II-1 | deceased | — | — | — | — | — | U |
| II-4 | 80 | — | — | — | — | — | U |
| II-5 | 70 | 1.2 | 0.9 | 2.28 | −6 | — | N |
| II-6 | 66 | 0.9 | 0.8 | 2.16 | −6 | — | N |
| II-7 | 68 | 1.3 | 1.1 | 1.9 | −2 | — | N |
| II-9 | 64 | 2.6 | — | 1.92 | −2 | −:AVS | U |
| II-11 | 61 | 1.6 | 1.4 | 1.6 | 0 | — | U |
| II-13 | deceased | — | — | — | — | + | A |
| III-1 | deceased | — | — | — | — | +:surgery | A |
| III-3 | 43 | 1.3 | na | — | −3 | — | N |
| III-4 | 41 | 1.2 | 0.8 | 2.52 | +4 | — | N |
| III-7 | 38 | 1.0 | 1.1 | 1.78 | −2 | — | N |
| III-8 | 37 | — | — | — | — | +:surgery | A |
| III-9 | 33 | 1.3 | 0.7 | 2.37 | −6 | — | N |

TABLE 1-continued

Phenotype Evaluations of SVAS Families

| Individual | Age | Ao Flow m/s | Po Flow m/s | Sinotubular Junction (cm.) | Impression Score | Cardiac Cath | Affected Status |
|---|---|---|---|---|---|---|---|
| III-11 | 32 | 1.5 | 1.2 | 2.8 | −3 | + | N |
| III-13 | 29 | 1.5 | 1.0 | 1.78 | +6 | +:SVPS | A |
| III-14 | 56 | 0.8 | 0.9 | 2.19 | −4 | — | N |
| III-15 | 52 | 1.8 | 0.9 | 1.8 | +3 | — | A |
| III-17 | 47 | — | — | — | — | +:surgery | A |
| III-19 | 41 | — | — | — | — | — | U |
| III-21 | 36 | 1.5 | 0.9 | 2.3 | −4 | — | N |
| III-22 | 27 | 1.4 | 0.9 | 2.0 | −5 | — | N |
| III-23 | 32 | 1.4 | 0.8 | 2.8 | −5 | — | N |
| III-24 | 30 | 2.0 | 0.6 | 1.87 | +3 | + | A |
| III-26 | 40 | — | — | 1.07 | +6 | +:surgery | A |
| III-28 | 33 | 1.6 | 0.8 | 2.1 | −4 | — | N |
| III-29 | 30 | 2.0 | — | 1.6 | −1 | −:BAV | U |
| III-30 | 37 | — | — | — | — | + | N |
| III-31 | 36 | — | — | — | — | + | N |
| III-32 | 34 | — | — | — | — | — | U |
| III-33 | 31 | — | — | — | — | + | A |
| III-34 | 29 | — | — | — | — | +:surgery | A |
| IV-1 | 25 | 1.4 | 1.0 | 1.8 | −2 | — | N |
| IV-2 | 23 | 1.8 | 0.7 | 2.6 | +2 | −:BAV | U |
| IV-3 | 12 | 1.3 | 0.8 | 1.71 | −3 | — | N |
| IV-4 | 18 | 1.6 | 1.1 | 2.4 | +1 | — | U |
| IV-5 | 14 | 1.0 | 1.0 | 1.98 | −6 | — | N |
| IV-6 | 16 | 1.8 | 1.1 | 1.86 | +1 | — | U |
| IV-7 | 2 | 1.0 | 1.0 | 1.37 | +1 | — | U |
| IV-8 | 9 | 2.5 | 0.9 | 1.27 | +5 | — | A |
| IV-9 | 7 | 1.1 | 0.7 | 1.8 | −4 | — | N |
| IV-10 | deceased | — | — | — | — | + | A |
| IV-11 | 21 | 1.2 | 1.0 | 2.79 | −5 | — | N |
| IV-12 | 18 | 1.4 | 1.0 | 1.87 | −2 | + | A |
| IV-13 | 3 | 3.3 | 2.2 | 1.01 | +6 | — | A |
| IV-14 | 11 | 1.4 | 0.8 | 1.7 | −6 | — | N |
| IV-15 | 10 | 1.1 | 1.0 | 1.69 | −3 | — | N |
| IV-16 | 4 mo | 1.7 | 1.7 | 0.72 | +4 | — | A |
| K1779 | | | | | | | |
| I-1 | 65 | — | — | — | +2 | — | A |
| II-1 | 41 | — | — | — | — | + | A |
| II-3 | 37 | — | — | — | — | — | U |
| II-4 | 33 | — | — | — | — | +:surgery | A |
| II-5 | 28 | — | — | — | — | — | U |
| III-1 | 16 | — | — | — | — | +:surgery | A |
| III-2 | 12 | 1.4 | 0.9 | 2.45 | −4 | — | N |

Doppler flow studies measured maximum aortic velocity (Ao) in m/s. Doppler flow studies also measured maximum pulmonary velocity (Po) in m/s. Impression scores were based on Doppler and two dimension echocardiographic findings. Affected individuals were noted as A, unaffected as N, and uncertain as U. No phenotypic data were available for individuals I-4 and III-32 (K1773) or II-3 and II-5 (K1779), so they were classified as uncertain.

Individual II-9 (K1773) was classified as uncertain because of aortic valvular stenosis (AVS). Individuals III-29 and IV-2 (K1773) were classified as uncertain due to bicuspid aortic valves (BAV).

FIG. 1 shows pedigree structure and elastin genotypes for SVAS families K1773 (FIG. 1A) and K1779 (FIG. 1B). Individuals having the characteristic pattern of elevated Doppler velocity and narrowing of the ascending aorta or pulmonary arteries on echocardiogram are represented by blackened circles (females) and squares (males). Unaffected individuals are represented by open squares or circles. Family members who have an equivocal phenotype or for whom no phenotypic data are available are represented by stippled squares and circles. Above each symbol, individual alleles are listed for the elastin polymorphic PCR marker. The disease gene cosegregates with the 244 bp allele (allele 2). Alleles shown in parentheses are inferred.

EXAMPLE 5

Linkage Analysis

A. Marker Linkage Data

To determine the chromosomal location of an SVAS gene, linkage analysis was performed using highly polymorphic DNA markers that span the genome. One hundred and forty markers were successfully scored and more than 28% of the genome was excluded (lod score −2 or lower) before linkage was identified.

Evidence for linkage was first identified using the marker pHHH232 (D7S395) (Table 2) (26). In K1773, the logarithm of the likelihood for linkage (lod score) was +2.47 at a recombination fraction (θ) of 0.001. For K1779, the pairwise lod score at this locus was +0.14, again at θ=0.001. The combined lod score for both families was +2.61. As pHHH232 had previously been mapped to the long arm of chromosome 7 (7q11), these data suggested that a gene for SVAS was located in that chromosomal region.

To improve the statistical support for these findings, linkage studies with two polymorphic markers known to be located near 7q11, pTHH28 (D7S371) and pIEF24.11 (D7S448) were performed (24, 25). A significant lod score of +4.78 (θ=0.001) was identified in K1773 with pIEF24.11. Combined lod scores were +1.12 for pTHH28 and +4.65 for pIEF24.11, strongly supporting the assignment of a SVAS gene to chromosome 7q.

The elastin gene is located near these polymorphic markers. To test whether elastin (ELN) could cause or be involved in the pathogenesis of SVAS, linkage analysis using a PCR-based polymorphic marker at the elastin locus (15) was performed. A lod score of +5.43 was obtained for K1773 and +0.50 for K1779, both at θ=0.001. These data confirm the localization of an SVAS gene to the long arm of chromosome 7 and support the involvement of elastin in the etiology of SVAS.

TABLE 2

Pairwise Lod Scores for K1773 and K1779

| | Recombination Fraction (Θ) | | | | | |
|---|---|---|---|---|---|---|
| | 0.001 | 0.05 | 0.1 | 0.2 | 0.3 | 0.4 |
| pElastin (ELN) | | | | | | |
| Kindred K1773 | +5.43 | +5.26 | +4.85 | +3.77 | +2.48 | +1.03 |
| Kindred K1779 | +0.50 | +0.42 | +0.35 | +0.21 | +0.09 | +0.02 |
| TOTAL | +5.93 | +5.68 | +5.19 | +3.98 | +2.57 | +1.05 |
| pHHH232 (D7S395) | | | | | | |
| Kindred K1773 | +2.47 | +2.25 | +2.03 | +1.52 | +0.94 | +0.35 |
| Kindred K1779 | +0.14 | +0.11 | +0.08 | +0.04 | +0.02 | +0.00 |
| TOTAL | +2.61 | +2.36 | +2.11 | +1.56 | +0.96 | +0.35 |
| pTHH28 (D7S371) | | | | | | |
| Kindred K1773 | +0.82 | +0.76 | +0.69 | +0.54 | +0.38 | +0.20 |
| Kindred K1779 | +0.30 | +0.25 | +0.20 | +0.11 | +0.05 | +0.01 |
| TOTAL | +1.12 | +1.01 | +0.89 | +0.65 | +0.43 | +0.21 |
| pIEF24.11 (D7S448) | | | | | | |
| Kindred K1773 | +4.78 | +4.44 | +4.04 | +3.15 | +2.11 | +0.95 |
| Kindred K1779 | −0.13 | −0.10 | −0.07 | −0.03 | −0.01 | 0.00 |
| TOTAL | +4.65 | +4.34 | +3.97 | +3.11 | +2.10 | +0.95 |
| pJ3.11 (D7S8) | | | | | | |
| Kindred K1773 | −7.57 | −3.47 | −2.31 | −1.16 | −0.56 | −0.20 |

Lod scores (pairwise) between SVAS and five chromosome 7 q markers (pELASTIN, pTHH28, pHHH232, pIEF24.11, pJ3.11) in three- and four-generation pedigrees. Lod scores have been calculated assuming autosomal dominant inheritance with a penetrance of 0.90 for both K1773 and K1779. When penetrance was varied from 0.60 to 0.95, maximum lod scores for K1773 and K1779 combined at Θ = 0.001 ranged from +5.52 to +5.81 for elastin, from +3.65 to +4.82 for pIEF 24.11, from +2.04 to +2.71 for pHHH232, and from +1.06 to +1.13 for pTHH28. Allele frequencies were estimated from the CEPH data base and from previous work (12–15). For purposes of this study, the frequency of this rare disease gene was estimated to be 0.001.

B. Multipoint Linkage Data

Although all four markers used in this study have been localized to the same region of chromosome 7 (15, 25, 26), the marker order is unknown. Determination of the order of these loci using the CEPH database was attempted, but marker order could not be determined with certainty as CEPH mapping data were either incomplete (pTHH28, pHHH232, pIEF24.11) or not done (elastin). Next, a determination of marker order was attempted, using data from SVAS families as these families were typed for elastin. Again, marker order could not be determined with certainty because the families were too small to yield significant marker-marker lod scores (greater than +3). Nevertheless, the best estimate of recombination distance between markers was consistent with linkage. The highest lod score was +2.7 at θ=0.06 between elastin and pIEF24.11. A multi-point analysis using these two markers was completed, and yielded a maximum lod score of +8.4 at the elastin locus. This substantial increase in lod score supports the assignment of an SVAS gene to the long arm of chromosome 7.

EXAMPLE 6

Methods for Translocation Analysis

A. Cell lines

Epstein-Barr virus transformed cell lines were established for each member of K1861 (20, FIG. 1C). Cells for isolation of total genomic DNA or for preparation of plugs for PFGE analysis were cultured in RPMI 1640 medium (Cellgrow/Mediatech) supplemented with 15% fetal calf serum (Hyclone). Human/rodent somatic cell DNAs for NIGMS mapping panel 1 were obtained from the Coriell Institute for Medical Research.

B. Southern Analysis

DNA restriction enzyme digestions were carried out as recommended by the manufacturer (New England Biolabs) with the exception that 2–5 fold excess enzyme was used. 5 ug of each digested DNA was separated on 0.7–1.0% agarose gels in 2× Tris-acetate buffer. Gels were depurinated for 10 min. in 0.25M HCl, rinsed briefly in $H_2O$, and soaked in 0.4N NaOH for 30 min. Transfer to nylon membranes (Hybond N+, Amersham) was carried out overnight in 0.4N NaOH (22). Following transfer the membranes were neutralized in 0.5M Tris-HCl (pH 7.0) for 10 min. and allowed to dry.

DNA for PFGE analysis was prepared in agarose plugs (30) and incubated with restriction enzymes in situ as recommended by the manufacturer (New England Biolabs). The resultant fragments were separated using contour clamped homogeneous electric field electrophoresis (CHEF) in a CHEF-DRII apparatus (Bio-Rad). Switch times were 13 to 150 sec for 27.3 hours. PFGE took place in 1.0% agarose gels using 0.5× TBE buffer. PFGE gels were transferred to nylon membranes as described above.

Radioactive DNA probes were prepared to high specific activity, $>2\times10^9$ cpm/ug DNA, by random hexamer priming as described by Feinberg and Vogelstein (23). Membranes were prehybridized for >2 hours in a solution containing 10% polyethylene glycol, 7% SDS, 1.5× SSPE and 500 ug/ml total human DNA. Hybridization was carried out in fresh solution following the addition of radiolabelled probe to $>1\times10^6$ cpm/ml. All hybridizations were performed at 65° C. for >8 hours. Filters were washed in 2× SSC/0.1% SDS for 10 min. at 25° C. followed by two washes in 0.1× SSC/0.1% SDS for 10 min. at 25° C. and a final wash in 0.1× SSC/0.1% SDS for 15 min. at 65° C. Filters were air dried and exposed to X-ray film (Kodak X-OMAT AR) overnight at −70° C. with two intensifying screens (Lightning Plus, Dupont).

C. PCR Amplification

DNA clone inserts, somatic cell hybrid DNA and total human DNA samples were amplified by the polymerase chain reaction (31). One hundred ng of genomic DNA or 10 ng of plasmid DNA was amplified in a 25 ul reaction containing 20 pmol of each oligonucleotide primer, 200 mM each of dCTP, dGTP, dTTP, and dATP, 1.5 mM MgCl12, 10 mM Tris (pH 8.3 at 20° C.), 50 mM KCl and 2 units of Taq polymerase (Boehringer Mannheim). Amplification conditions were 94° C./10 min followed by 30 cycles of 64° C./60 sec, 72° C./60 sec and 94° C./60 sec. Three PCR primer sets were synthesized for this study. Chromosome 6 specific primer sequences from the translocation breakpoint region were:

T6F: 5'-GGAGAGAGCCAGGCAATGC-3' (SEQ ID NO:3);

T6R: 5'-AAAATGCGCAGGGCATTGCCAA-3' (SEQ ID NO:4).

Chromosome 7 specific primer sequences were:

T7F: 5'-CCTGGACTTGGAGTTGGTGCTGG-3' (SEQ ID NO:5);

T7R: 5'-CCGAGCCCTCCAAGGACC-3' (SEQ ID NO:6).

Primers for amplification across the translocation breakpoint were:

TBF: 5'-ATCGTTCAGAAATGGAACACTCA-3' (SEQ ID NO:7);

TBR: 5'-ACCTGGACCCGCGGTTAACTTA-3' (SEQ ID NO:8).

D. Genomic Library Construction and Screening

Genomic phage libraries of translocation patient III-1 were constructed in lambda FIX II (Stratagene) according to the manufacturer's recommendations. Approximately 2×10$^5$ primary recombinants were incubated with *E. coli* strain LE392 and plated at low density. Duplicate plaque lifts were made with 0.2 um Biotrans filters (ICN) by the method of Benton and Davis (32). Prehybridization of library filters was carried out in an aqueous solution consisting of 5× SSPE, 5× Denhardt's solution, 0.5% SDS and 500 ug/ml sheared, denatured salmon sperm DNA for >2 hr. Hybridization was carried out in fresh hybridization solution following the addition of radiolabelled probe DNA to >2×10$^6$ cpm/ml. Hybridization was performed overnight at 65° C. Filter washes consisted of one 25° C. wash in 2× SSC/0.1% SDS for 15 min. followed by one 25° C. washes in 0.1× SSC/0.1% SDS for 15 min. and a final 65° C. wash in 0.1× SSC/0.1% SDS for 5 min.

E. DNA Constructs and Sequencing

Elastin cDNA probes were cloned from human cDNA using PCR. The oligonucleotide primers used in these cloning experiments were derived from published sequence data (33, 34). These primers were:

ELN1F: 5'-AGATGGCGGGTCTGACGG-3' (SEQ ID NO:9);

ELN2F: 5'-TCCCAGGAGCTCGGTTCCCCG-3' (SEQ ID NO:10);

ELN3R: 5'-CACCTGGGATCCCAGCAGGTG-3' (SEQ ID NO:11);

ELN4R: 5'-GGCCACAAGCTTTCCCCAGGCA-3' (SEQ ID NO:12).

Clones generated by PCR spanned bases 513–2229 of the mature cDNA.

DNA fragments from genomic phage were isolated and subcloned into pBluescript II SK(−) (Stratagene) as described (35). Clones N-3.0 and N-2.0 were constructed by digesting genomic N-type pkage with Hind III, followed by gel purification of the appropriate fragments and ligation into Hind III digested pBluescript II SK(−). Clones N-2.8 and T1-14 were prepared by digesting N or T1 genomic phage with Hind III (genomic site) and Not I (phage vector site), gel purification of correct size fragments and ligation into pBluescript II SK(−). Plasmid DNAs were isolated from *E. coli* cultures by the alkaline lysis method and purified by centrifugation through CsCl gradients (35). Sequencing of double stranded DNA templates was carried out using the dideoxy chain termination method (36) employing the Sequenase 2.0 kit (US Biochemicals). Sequence alignment was done using the Intelligenetics program suite running on a Sun workstation. Sequence analysis was performed using the FastDB algorithm of the IG Suite and through the BLAST server at NCBI (37).

EXAMPLE 7

Translocation Analysis

A. Identification of anomalous restriction fragments in DNA from SVAS patients

Figure 3A:
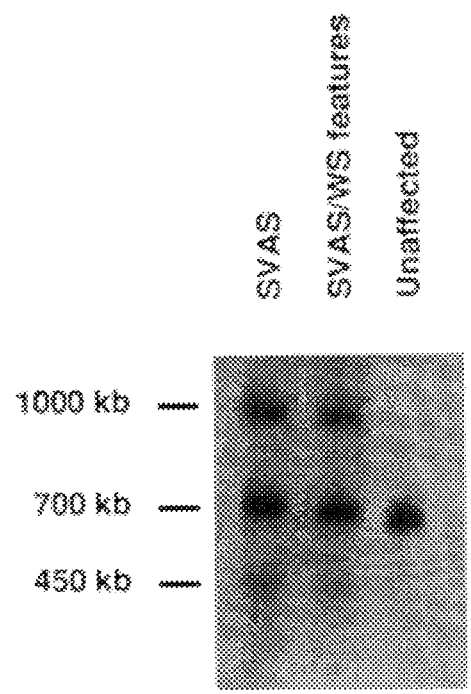
FIG. 3A shows that hybridization of a full-length elastin cDNA probe to Not I digests of DNA from SVAS patients II-1 (affected with SVAS) and III-2 (affected with SVAS and phenotypic features of Williams syndrome) reveals aberrant restriction fragments of 450 and 1000 kb. The 700 kb fragment is seen in both unaffected (individual I-1) and affected members of kindred 1861 and represents the normal allele.

To test whether a t(6:7)(p21.1;q11.23) balanced translocation identified in a patient with SVAS disrupts the elastin locus, elastin cDNA and genomic probes were generated to screen for anomalous restriction fragments in DNA from members of SVAS kindred 1861 (FIG. 1C). High molecular weight DNA extracted from lymphoblastoid cells of affected and unaffected family members was incubated with the infrequently cutting restriction enzyme Not I. The resultant restriction fragments were separated by pulsed field gel electrophoresis (PFGE) and transferred to nylon membranes. Hybridization with an elastin cDNA probe revealed Not I fragments of 1000 kb, 700 kb and 450 kb in affected members of kindred 1861 (FIG. 3A). By contrast, in unaffected members of this family and in control individuals, only the 700 kb Not I fragment was observed. These additional fragments are thus unlikely to be neutral polymorphisms or the result of variable methylation. These data suggest that the SVAS-associated translocation disrupts the elastin gene, producing novel Not I restriction fragments. Alternatively, the translocation may disrupt sequences near the elastin locus, but not disrupt the elastin gene itself. It is unlikely that these aberrant fragments are caused solely by a deletion or an insertion since the elastin cDNA identified two anomalous fragments, one larger (1000 kb), and one smaller (450 kb) than the fragment observed in controls.

Figure 3B:
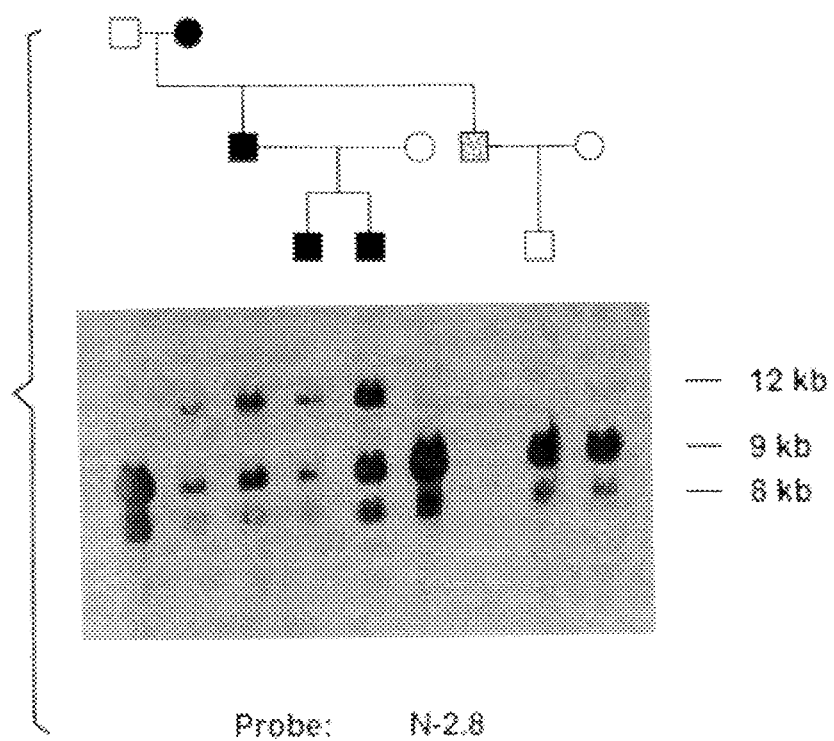
FIG. 3B shows that hybridization of a 2.8 kb elastin genomic probe (N-2.8) to Bam HI digests of DNA from members of K1861 reveals 12 kb aberrant fragments in SVAS patients. Pedigree information is identical to panel A. The probe N-2.8 also hybridizes with two Bam HI fragments of 8 kb and 9 kb in both affected and unaffected individuals of K1861. These fragments represent the normal elastin allele. The aberrant fragment was not seen in DNA samples from 100 controls.

To confirm these findings and to determine how close the SVAS-associated translocation breakpoint is to the elastin gene, these experiments were repeated using restriction enzymes that cut human genomic DNA more frequently. Elastin cDNA probes identified anomalous Bam HI, Hind III and Eco RV restriction fragments of 12 kb, 2 kb and 5 kb respectively, in affected family members but not in unaffected members. A 2.8 kb genomic probe derived from the 3' end of the elastin gene (N-2.8) also identified the anomalous Bam HI restriction fragments of 12 kb in affected family members but not in unaffected members (FIG. 3B). The 12 kb anomalous Bam HI fragment was not observed in DNA samples of more than 100 unrelated control individuals, suggesting that it is not a neutral polymorphism. These findings confirm PFGE data and indicate that the SVAS-associated translocation disrupts sequences very near the elastin locus.

B. The SVAS-associated translocation disrupts the elastin gene

Figure 4A:
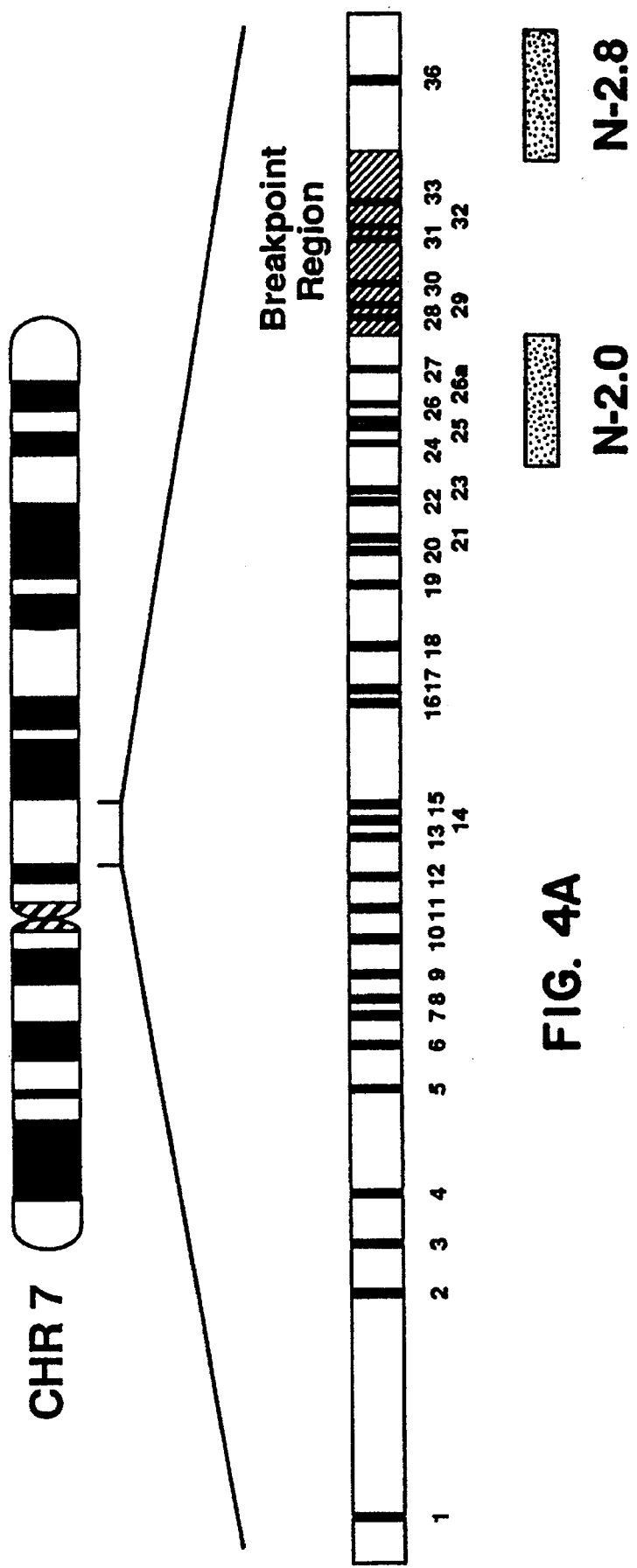
FIGS. 4A–4B shows PFGE analyses of DNA from kindred 1861.
Figure 4B:
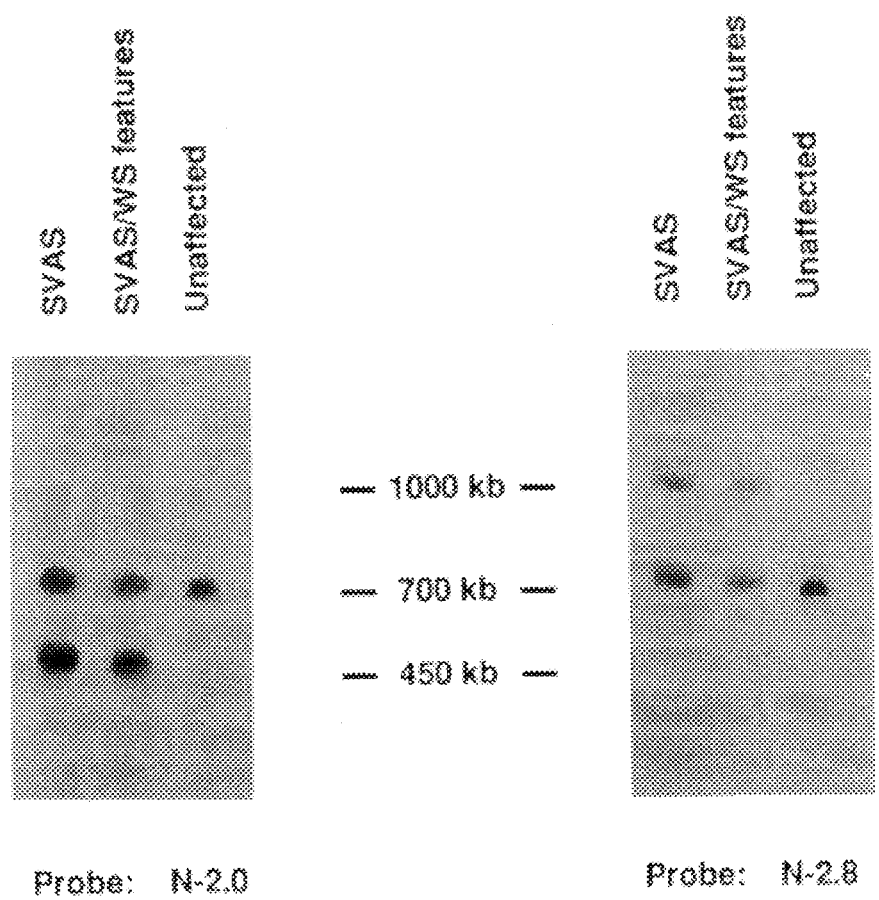

If the germline translocation identified in SVAS kindred 1861 disrupts the elastin gene, probes from either end of that locus should detect different anomalous restriction fragments, each derived from one of the two translocation chromosomes. To test this hypothesis, genomic subclones from different regions of the elastin gene were used to probe filters of DNA from affected and unaffected family members after digestion with Not I (FIG. 4A). In affected members of this family, a 2.0 kb elastin genomic probe encompassing exons 24–27 (N-2.0) detected the 450 kb anomalous Not I fragment (FIG. 4B, left). By contrast, an elastin probe containing exon 36 (N-2.8) defined the 1000 kb anomalous Not I fragment (FIG. 4B, right). Both probes also hybridized to the normal 700 kb Not I fragment in affected family members, unaffected members and controls (FIG. 4B). As noted above (FIG. 3A), a full-length elastin cDNA probe detected all three Not I fragments in affected members of this family. These data show that the SVAS-associated translocation lies within the elastin gene.

Figure 5A:
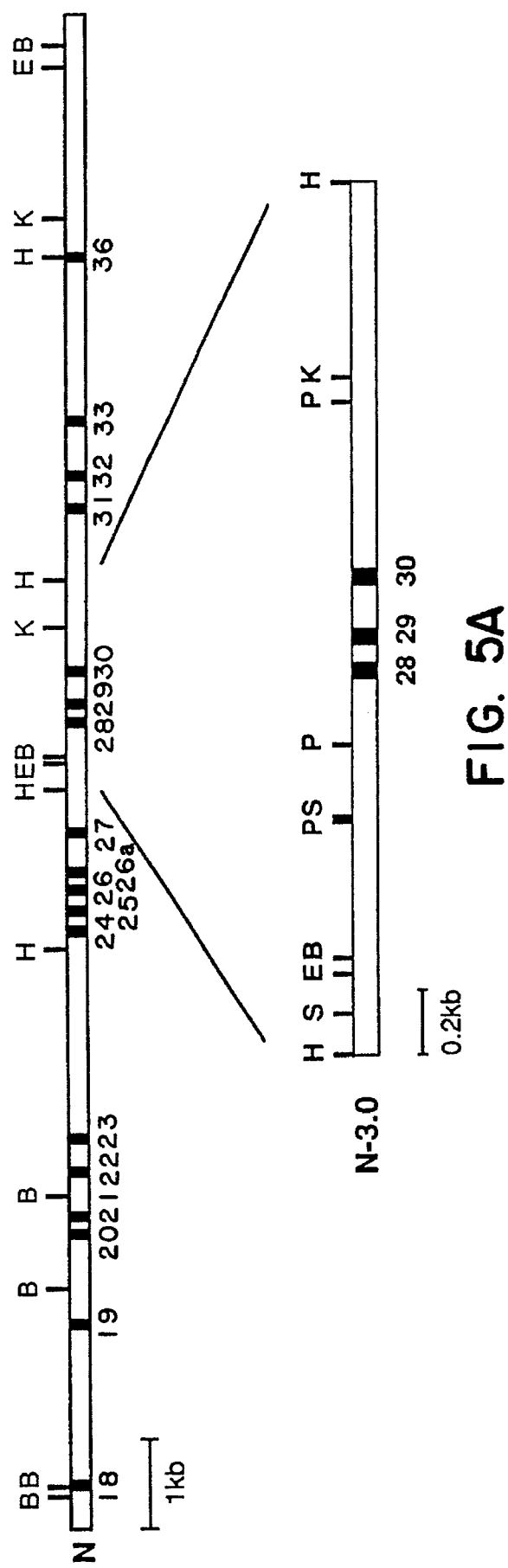
FIGS. 5A–5B show restriction maps of the T1 translocation allele.
Figure 5B:
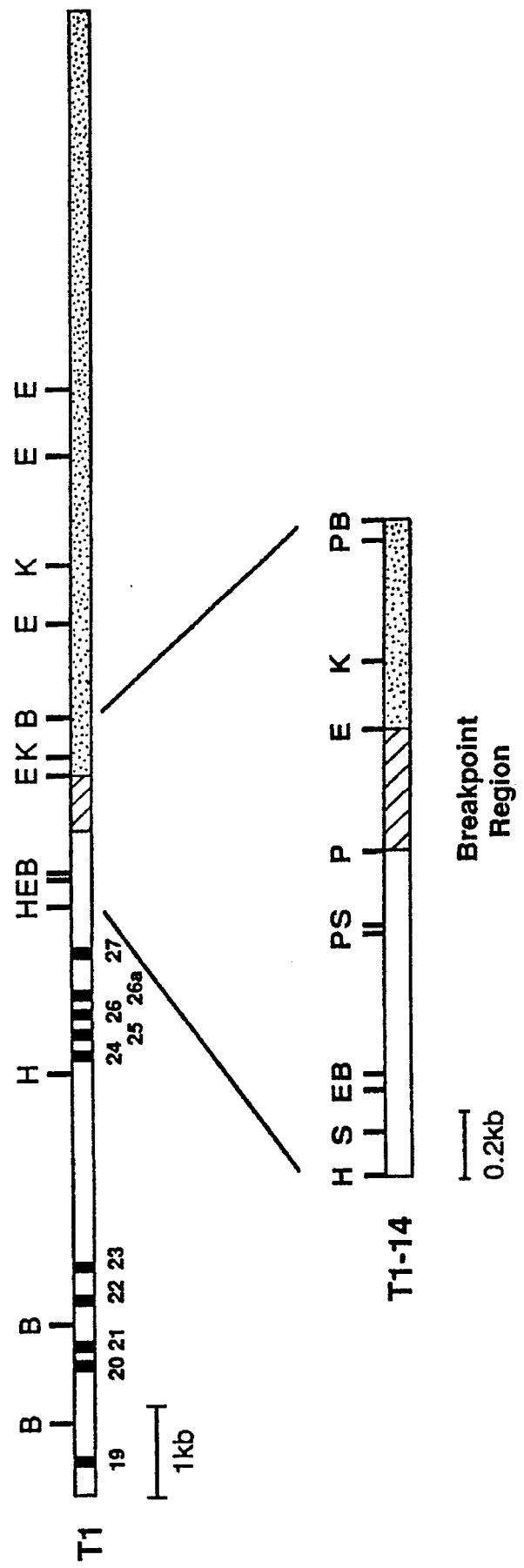

To confirm this finding and refine the location of the translocation breakpoint, a bacteriophage library was generated from partially cut, size-selected DNA obtained from individual III-1 of kindred 1861 (FIG. 1C), an affected child who had undergone surgery for correction of SVAS. When an elastin cDNA subclone spanning exons 18–36 was used to screen this library, two classes of clones were identified, N and T1. Restriction maps of class N clones (FIG. 5A) were consistent with published maps of the elastin locus (38, 39). These clones represent this patient's nontranslocated elastin allele. Restriction maps from the T1 clone identified some shared fragments with N-type clones and published maps, but the T1 map diverged significantly at the 3' end, resulting in approximately 12.7 kb of DNA which does not correspond to restriction maps of the elastin locus (FIG. 5B). The likely explanation for these restriction mapping data is that T1 represents a translocation allele containing elastin sequences from chromosome 7 as well as chromosome 6 sequences, resulting in novel restriction sites.

To test whether T1 contains a translocation breakpoint, Hind III fragments from both N and T1 were subcloned and sequenced. Directed sequence analyses and restriction mapping (FIG. 5A and 5B) of shared fragments showed that N and T1 both contained elastin exons 19–27. However, in 3' sequences these clones diverge; N clones contained elastin exons 28–36 (FIG. 5A) whereas PCR and sequence analysis failed to detect elastin exons in the 12.7 kb of divergent T1 DNA (FIG. 5B). Instead, sequences derived from this subclone mapped to chromosome 6, as determined by PCR analyses of a panel of DNA samples from chromosome-specific somatic cell hybrids (Table 3). These data indicate that clone T1 is one of the germline alleles derived from the t(6;7)(p21.1;q11.23) balanced translocation and suggest that the SVAS-associated translocation disrupts the elastin gene near exon 28 (FIG. 5B).

TABLE 3

Somatic Cell Hybrid Mapping of Sequences Flanking the Translocation Breakpoint

| Chromosome | Concordant Hybrids | | Discordant Hybrids | | % |
| | +/+ | –/– | +/+ | –/– | Discordant |
| --- | --- | --- | --- | --- | --- |
| (1) Segregation of T7F + T7R with Human Chromosomes in Human-Rodent Mapping Panel | | | | | |
| 1 | 4 | 6 | 0 | 8 | 45 |
| 2 | 5 | 5 | 1 | 7 | 45 |
| 3 | 8 | 4 | 2 | 4 | 34 |
| 4 | 9 | 4 | 2 | 4 | 28 |
| 5 | 6 | 3 | 3 | 6 | 50 |
| 6 | 9 | 3 | 3 | 3 | 34 |
| 7 | 12 | 6 | 0 | 0 | 0 |
| 8 | 11 | 4 | 2 | 1 | 17 |
| 9 | 0 | 6 | 0 | 12 | 66 |
| 10 | 6 | 3 | 3 | 6 | 50 |
| 11 | 6 | 5 | 1 | 6 | 39 |
| 12 | 8 | 4 | 2 | 4 | 34 |
| 13 | 6 | 4 | 2 | 6 | 44 |
| 14 | 10 | 4 | 2 | 2 | 22 |
| 15 | 11 | 5 | 1 | 1 | 11 |
| 16 | 1 | 5 | 1 | 11 | 66 |
| 17 | 12 | 3 | 3 | 0 | 17 |
| 18 | 7 | 5 | 1 | 5 | 33 |
| 19 | 7 | 4 | 2 | 5 | 39 |
| 20 | 10 | 5 | 1 | 2 | 17 |
| 21 | 5 | 3 | 1 | 7 | 55 |
| 22 | 6 | 4 | 2 | 6 | 44 |
| X | 2 | 5 | 1 | 10 | 61 |
| Y | 4 | 5 | 1 | 8 | 44 |
| (2) Segregation of T6F + T6R with Human Chromosomes in Human-Rodent Mapping Panel | | | | | |
| 1 | 4 | 6 | 8 | 0 | 45 |
| 2 | 5 | 5 | 7 | 1 | 45 |
| 3 | 8 | 4 | 4 | 2 | 34 |
| 4 | 10 | 5 | 2 | 1 | 17 |
| 5 | 8 | 4 | 4 | 2 | 34 |
| 6 | 12 | 6 | 0 | 0 | 0 |
| 7 | 9 | 3 | 3 | 3 | 34 |
| 8 | 11 | 4 | 1 | 2 | 17 |
| 9 | 0 | 5 | 12 | 1 | 72 |
| 10 | 8 | 5 | 4 | 1 | 28 |
| 11 | 6 | 5 | 6 | 1 | 39 |
| 12 | 9 | 4 | 3 | 2 | 28 |
| 13 | 7 | 5 | 5 | 1 | 34 |
| 14 | 11 | 4 | 1 | 2 | 17 |
| 15 | 9 | 4 | 3 | 2 | 28 |
| 16 | 3 | 5 | 5 | 1 | 56 |
| 17 | 12 | 3 | 0 | 3 | 17 |
| 18 | 7 | 5 | 5 | 1 | 34 |
| 19 | 9 | 6 | 3 | 0 | 17 |
| 20 | 9 | 4 | 3 | 2 | 34 |
| 21 | 7 | 4 | 5 | 2 | 39 |
| 22 | 8 | 5 | 4 | 1 | 28 |
| X | 2 | 4 | 10 | 2 | 67 |
| Y | 3 | 4 | 9 | 2 | 61 |

C. Sequence analysis of the T1 translocation breakpoint

To prove that T1 represents a translocation allele, the divergent restriction fragments were subcloned and sequenced. Refined restriction mapping of the 3 kb Hind III fragment from N (subclone N-3) and the 14 kb of T1DNA containing divergent sequences (subclone T1-14), demonstrated that these fragments share ~1.3 kb of DNA and then diverge. To characterize this divergence more completely, sequence analyses of N and T1 subclones near the breakpoint were performed. The sequences of N-3 and T1-14 are identical only for 1337 bases (FIG. 6). The point of divergence represents the translocation breakpoint and lies within elastin exon 28. The rearrangement encodes a new stop codon 6 bp downstream of the breakpoint (FIG. 6). No significant other open reading frames were identified within 1 kb of the breakpoint; moreover, a second in-frame stop codon was identified 129 bp downstream of the first stop codon.

Figure 7A:
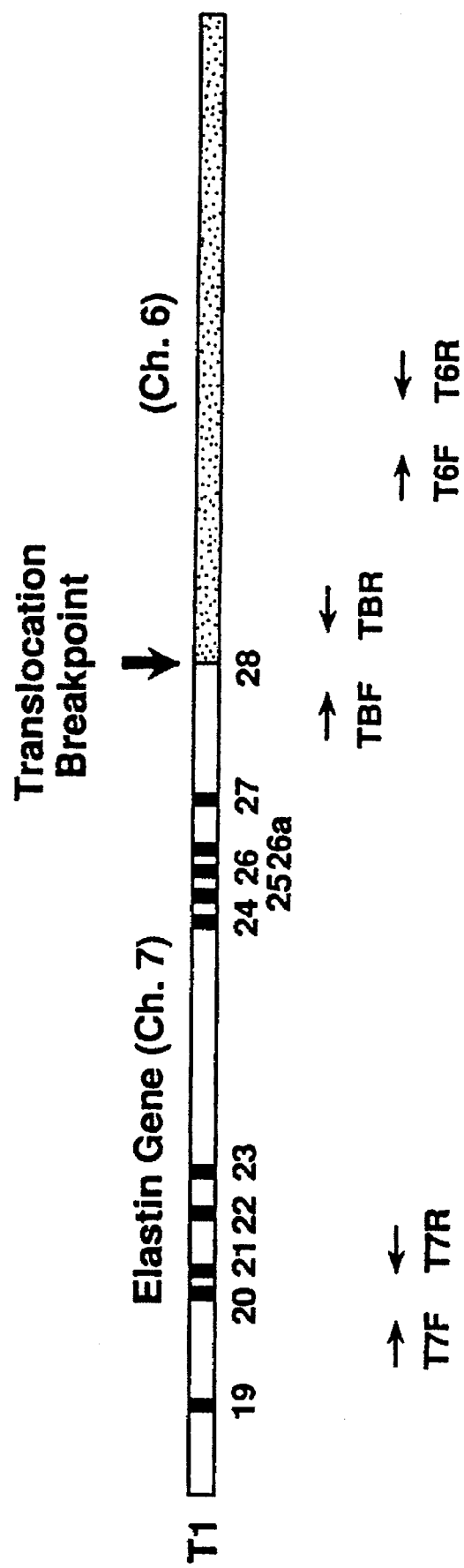

To confirm that clone T1 represents a translocation allele and is not an artifact of cloning, oligonucleotide primer pairs were constructed for PCR analysis of the putative breakpoint (FIG. 7A). These primers produced a product of the predicted size in PCR reactions performed using template DNA from T1 and with genomic DNA of members of kindred 1861 who carry the SVAS-associated translocation (FIG. 7B). By contrast, identical amplification conditions using DNA from unaffected family members and controls gave no product with these primers. As expected, primers generated from sequences on either side of the breakpoint yielded PCR products of the predicted size from all subjects. Analyses of somatic cell hybrid mapping panels showed that sequences on one side of the breakpoint mapped to chromosome 7 whereas sequences on the other side of the breakpoint mapped to chromosome 6 (Table 3). These data indicate that sequences derived from clone T1 represent one of the two translocation alleles and prove that the breakpoint disrupts one elastin allele.

D. Characterization of the translocation in a family member with SVAS and features of Williams syndrome All affected members of kindred 1861 had isolated SVAS with one exception; individual III-2 had SVAS, full cheeks, a hoarse voice and bilateral fifth finger clinodactyly, all features seen in Williams syndrome. One possible mechanism for this phenotypic variation is instability of the translocation chromosome, resulting in a more severe mutation of the elastin gene or involvement of a second gene. However, PFGE and Southern analyses indicated that the anomalous restriction fragments identified in individual III-2 were identical to the anomalies found in other affected family members (FIGS. 3B and 3C). Furthermore, PCR analyses of the translocation allele in this patient showed products of the identical size as other family members with the translocation (FIG. 7B). To confirm that these mutations were identical, PCR was used to clone and sequence the translocation breakpoint from individual III-2. The translocation sequences in this individual were identical to those identified previously. These data indicate that the additional features of Williams syndrome seen in individual III-2 of this SVAS family are not due to instability at the translocation locus.

EXAMPLE 8

Methods for Mutation Analysis

Phenotypic evaluations were performed as described above. DNA analysis was performed as described in Example 2 except that the markers used in probing were genomic clones for elastin: 5-9, 5-2, 5-3, 5-4, 5-2.6, a large elastin phage clone 5, and elastin cDNA.

Pulsed field gel electrophoresis were performed as follows. Plugs were made from $1 \times 10^8$ cells from established lymphoblastoid cell lines. Cells were resuspended in NET (0.1M EDTA, 20 mMNaCl, 10 mM Tris pH 7.5) and 1% low melt agarose in NET. Plugs were incubated overnight with 10 mg proteinase K, 0.45M EDTA, 0.9 mM Tris pH 7.5, and 1% sarcosyl. Plugs were washed over 4 days in TE-3 followed by TE-4. Plugs were then digested with Not I according to manufacturer's conditions in 200 ul total volume with spermidine. Plugs were run on a Biorad CHEF field gel apparatus in 1% LE agarose in 0.5×TBE (20×TBE: 0.9M Trizma Base, 0.9M Boric Acid, 20 mM EDTA) at 14° C. Running conditions were initial A time, 13 sec; final A time, 150 sec.; start ration 1; run time, 27.3 hours; 200 volts. Probing conditions were identical to those described.

Genomic phage and cosmid libraries of high molecular weight DNA from K2049 individual II-2 were constructed in lambda DASH II strategies as described in Example 6 except that approximately $1 \times 10^5$ primary recombinants were incubated with E. coli strain LE392 and two 25° C. washes in 0.1×SSC/0.1% SDS performed. DNA fragments from genomic phage were subcloned into pBSSK+ (Stratagene) and sequenced as described in Example 6.

EXAMPLE 9

Mutation Analysis

A. Identification of PFGE and Southern anomalies in DNA from SVAS patients

Figure 9A:
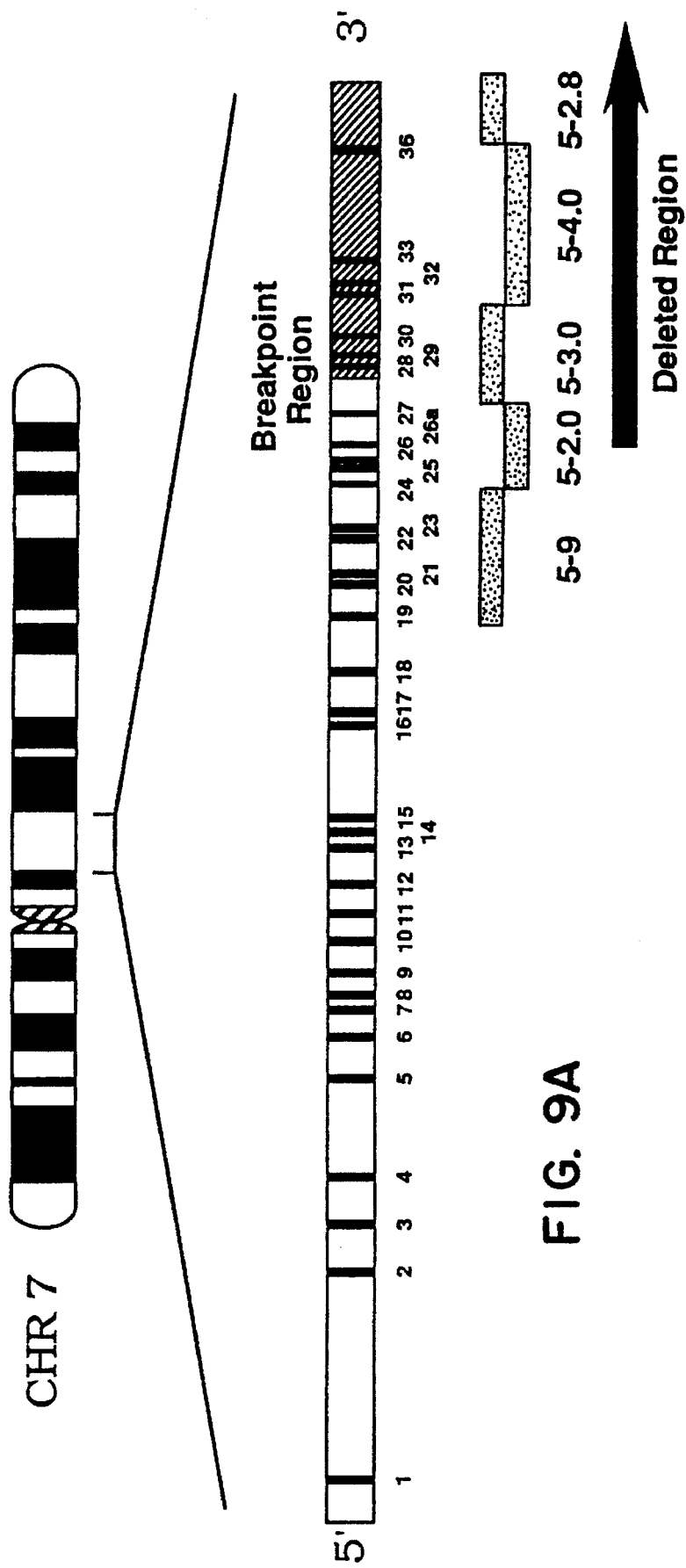
FIG. 9A shows the chromosomal map of the elastin locus showing the intron and exon structure and the location of probes used to define the SVAS-associated mutation. The predicted location of the mutation is shown.
Figure 9B:
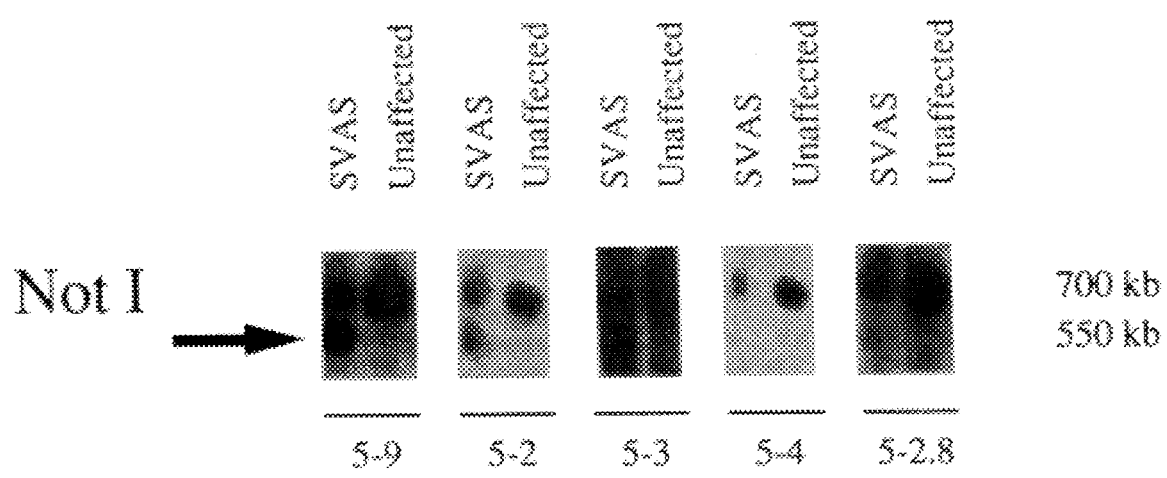
FIG. 9B shows that several 5' elastin probes detect a 550 kb anomalous Not I fragment in DNA from affected members of K2049. By contrast, 3' probes fail to detect a Not I anomaly. All probes detect the normal 700 kb Not I fragment which is also seen in unaffected members of this kindred. These data indicated that 3' elastin sequences are deleted in affected members of this SVAS family.

An elastin cDNA probe was used to screen for anomalous restriction fragments in DNA from members of SVAS K2049, a two generational family with two affected individuals from Nevada (FIG. 1D). High molecular weight DNA extracted from lymphoblastoid cells of affected and unaffected family members was incubated with the restriction enzyme, Not I. The resultant restriction fragments were separated by pulsed field gel electrophoresis (PFGE) and transferred to nylon membranes. Hybridization with a full-length elastin phage clone revealed Not 1 fragments of 700 kb and 550 kb in both affected members of K2049 (FIG. 9B). By contrast, in unaffected members of this family and in controls, only the 700 kb Not I fragment was observed. These anomalous restriction fragments were not identified in DNA from controls, so they are unlikely to be neutral polymorphisms or the result of variable methylation. These data suggest that an SVAS-related mutation is located near the elastin locus.

To confirm these findings and to determine how close the SVAS-associated DNA anomalies are to the elastin gene, these experiments were repeated using Southern analysis. An elastin cDNA probe identified anomalous Bcl I restriction fragments of 8.5 kb in affected family members but not in unaffected members (FIG. 8). The 8.5 kb Bcl I fragment was not observed in DNA samples of more than 100 unrelated control individuals, suggesting that it is not a neutral polymorphism. These findings confirm PFGE data indicating that the SVAS-associated mutation disrupts sequences near the elastin locus. Possible mutations that could explain these data include Bcl I and Not I site polymorphisms, a deletion, an insertion, an inversion or a translocation.

B. The SVAS-associated mutation disrupts the elastin gene

To define the location and character of the SVAS-associated mutation, genomic subclones that span the 3' half of the elastin gene (FIG. 9A) were used to probe Not I filters of DNA from affected and unaffected family members. In affected members of this family, the 5' elastin probes (5-9, 5-2, 5-3) detected the 550 kb anomalous Not I fragment (FIG. 9B) and the 700 kb fragment which was also detected in unaffected family members and in controls. By contrast, the 3' elastin probes (5-4, 5-2.6) identified only the 700 kb Not I fragment in both affected and unaffected family members (FIG. 9B). These data suggest that the SVAS-associated mutation is a deletion affecting sequences in the 3' region of the elastin gene.

EXAMPLE 10

Coinheritance of an Elastin Null Allele and Williams Syndrome

To determine if mutations in the elastin gene cause or are involved in the pathogenesis of Williams syndrome, elastin cDNA and genomic clones were used to screen for anomalous restriction fragments in DNA from individuals with Williams syndrome.

DNA extracted from lymphoblastoid cells of affected and unaffected individuals was incubated with the restriction enzyme Pst I. The resultant restriction fragments were separated by agarose gel electrophoresis and transferred to nylon membranes. Hybridization with an elastin genomic probe revealed Pst I fragments of 3.5, 1.3, and 1.2 kb in an affected member of kindred 1806 (individual II-1, FIG. 10). By contrast, in DNA from controls, Pst I fragments of 2.0 and 1.6 kb were also observed and the 3.5 kb fragment was uncommon (8/100). Since no additional restriction fragment anomalies were identified with this probe in DNA from this patient, the 3.5 kb Pst I fragment represents a site polymorphism. The absense of 2.0 and 1.6 kb Pst I fragments in this individual can be explained by homozygosity for this uncommon polymorphism or by hemizygosity at the elastin locus.

Figure 11E:
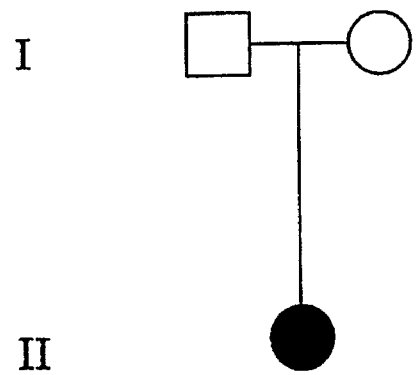
FIG. 11 shows pedigree structure for Williams syndrome kindreds. Individuals with the characteristic features of Williams syndrome are indicated by filled circles (females) or squares (males). Empty circles or squares indicate unaffected individuals. In kindred 1806 (FIG. 11A) and Kindred 2C42 (FIG. 11B), the Williams phenotype is transmitted from parent to child. Kindreds 1998 (FIG. 11C) and 2016 (FIG. 11D), 2767 (FIG. 11E), 1866 (FIG. 11F), 1868 (FIG. 11G) and 1888 (FIG. 11H) represent sporadic cases of Williams syndrome. Hemizygosity at the elastin locus was demonstrated in all affected members of these kindreds by Southern and PCR analyses, proving that mutations in the elastin gene cause Williams syndrome.
Figure 11F:
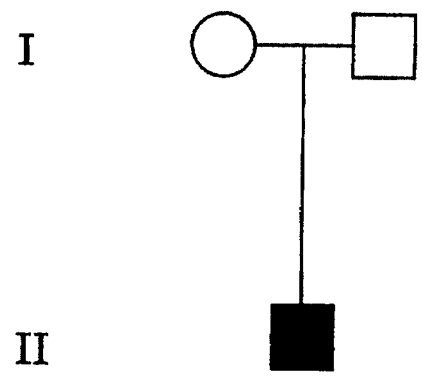
Figure 11G:
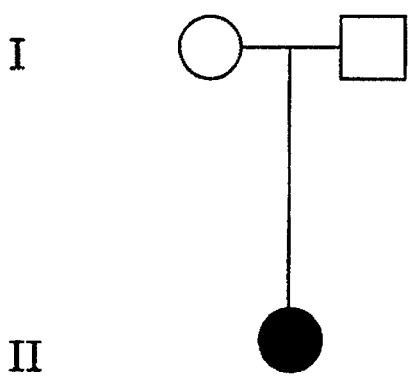
Figure 11H:
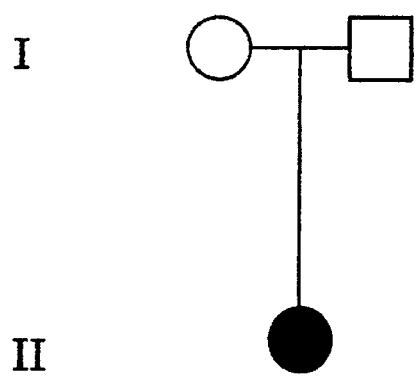

To determine if Williams syndrome patient II-1 was hemizygous at the elastin locus, DNA samples from the rest of kindred 1806 (FIG. 11A) were examined. This kindred is unusual in that it shows father to son transmission of the Williams syndrome. Hybridization of the elastin genomic clone to DNA from these family members showed that the phenotypically unaffected grandmother (individual 1—1, FIG. 10) was heterozygous at this marker locus, showing both the uncommon 3.5 kb fragment as well as the common 2.0 and 1.6 kb Pst I fragments. Unfortunately, the grandfather (individual I-2) was not available for phenotypic or genotypic analyses, so the pattern of inheritance could not be determined. However, the affected son (individual III-1) of the Williams patient (individual II-1) failed to inherit the 3.5 kb Pst I fragment from his father; he only inherited the 2.0 and 1.6 kb fragment from his mother. Since this family showed typical codominant inheritance of informative polymorphic markers from four different genomic loci, it is very unlikely (likelihood <1/1000) that these findings are due to false paternity. Rather, these data indicate father to son transmission of a null allele at the elastin locus and suggest that hemizygosity at the elastin locus may cause Williams syndrome.

EXAMPLE 11

Hemizygosity at the Elastin Locus in Williams syndrome

To determine if hemizygosity at the elastin locus is important in the pathogenesis of Williams syndrome, polymorphic markers at this locus were used to screen for null mutations in DNA samples from additional patients from Kindreds 1998, 2016, 2767, 1866, 1868 and 1888 (FIGS. 11C-11H, respectively). These experiments showed that individuals with sporadic Williams syndrome failed to inherit an elastin allele from a parent. DNA analyses with highly informative polymorphic markers from four different loci showed the expected pattern of codominant inheritance in all families, indicating that these findings were not due to misinheritance or DNA sampling errors. Instead, these observations can be explained only by hemizygosity at the elastin locus. Since all parents were heterozygous at the elastin locus, hemizygosity in their affected children resulted from de novo mutations. Finally, parent to child transmission of a null mutation at the elastin locus was discovered in a second family with Williams syndrome (K2042, FIG. 11B). These data indicate that hemizygosity at the elastin locus is responsible for Williams syndrome in these individuals.

To summarize, the above Examples demonstrate that a gene for SVAS is located on the long arm of chromosome 7, near elastin. No recombination between elastin and the disease phenotype was observed suggesting that elastin is the SVAS gene. The Examples further demonstrate linkage between SVAS and a polymorphism within the elastin gene. The Examples also show that a heritable translocation in a family with SVAS disrupts the elastin gene, demonstrating that a mutation in elastin sequences causes or is involved in the pathogenesis of SVAS in this family. The Examples show that a deletion in the 3' end of the elastin gene cause SVAS in another family. Finally, the Examples show that mutations in the elastin gene also cause or are involved in the pathogenesis of Williams syndrome.

Figure 12:
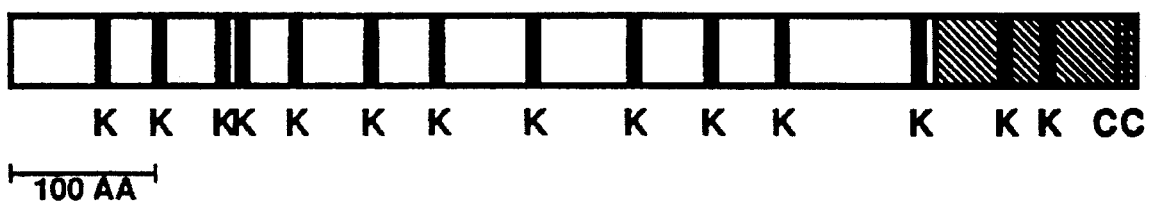
FIG. 12 shows predicted amino acid structure of the elastin protein showing potential sites for desmosine crosslinking (K) and disulfide bridging (C).

It is not yet clear whether the pathologic features of SVAS result from quantitative or qualitative defects in elastin. This protein is a highly hydrophobic, nonglycosylated polypeptide of approximately 830 amino acids and is thought to form a random coil. After secretion, individual elastin molecules are covalently cross-linked to one another via lysine residues by the copper-dependent enzyme, lysyl oxidase, to form a complex interlocking network of elastic fibers (40). The heritable translocation described here disrupts the elastin gene at exon 28, resulting in a new stop codon 6 bp downstream of the breakpoint. It is not known if this mutant elastin allele is expressed; but, if it is, the resultant protein would lack two consensus sites for desmosine cross-linking and two conserved cysteine residues near the carboxyl terminus (FIG. 12). These cysteine residues are thought to be important for interaction with the cysteine-rich protein fibrillin in arrays of microfibrils. A truncated protein lacking domains critical for intermolecular interaction might have a dominant-negative effect on elastin encoded by the normal allele, disrupting post-translational processing and development of elastic fibers. Alternatively, the mechanism of SVAS may involve a quantitative loss of normal elastin resulting from reduced production or stability of mRNA or protein. In this case, the pathologtc changes seen in SVAS would result from adaptation of an inelastic vessel to hemodynamic stress from recurrent injury and repair.

The mechanism of vascular stenosis in SVAS involves increased hemodynamic damage to the endothelium of inelastic arteries, causing intimal proliferation of smooth muscle and fibroblasts and eventual fibrosis. This mechanism is supported by clinical improvement of pulmonary artery stenosis seen in SVAS patients after postnatal reduction of pulmonary artery pressure. By contrast, narrowing of the aorta generally progresses over time, coincident with sustained increases in systemic blood pressure after birth.

It is intriguing to note that some of the pathologic features of SVAS are also seen in atherosclerotic vessels. Intimal proliferation of vascular smooth muscle and fibroblasts with subsequent fibrosis also appears to be a critical feature of the atherogenic process. With time, atherogenesis may also affect the architecture of the media of a vessel, including the elastic elements. The present data show that abnormalities in structural proteins, like elastin, that comprise the arterial wall play a role in vascular disease and indicate that these proteins are targets for therapy.

Although elastin is found in the extracellular matrix of many organs, previously studied SVAS patients have no obvious abnormalities of skin, lungs and other distensible tissue. The reasons for this observation are not known. Differential expression of a family of elastin genes could account for this finding, but only one elastin gene has been identified (29). Clinical and pathologic studies of SVAS patients have focused on the vascular system, so it is possible that abnormalities of other tissues have been overlooked (41). Alternatively, the complex structure of elastic fibers in the vascular system may be more sensitive to subtle mutations in the elastin gene.

Studies showing identical vascular pathology in SVAS and Williams syndrome have suggested that these disorders are related. Patients have been identified with Williams syndrome features in autosomal dominant SVAS families (42). The SVAS genotype cosegregated with the Williams phenotype in these patients, a finding not likely due to chance. The present studies show that hemizygosity at the elastin locus is responsible for Williams syndrome and that SVAS and Williams syndrome are allelic disorders.

These studies have practical implications for treatment of this vascular disorder. Currently, the only treatment option for SVAS is vascular surgery, a procedure that has significant morbidity and mortality. Since increased hemodynamic stress on inelastic arteries causes vascular obstruction in SVAS, reduction of this stress will ameliorate the problem. Existing pharmacologic agents, like beta-adrenergic blockers, reduce heart rate and blood pressure and will prove effective in SVAS.

Genetic variants in the elastin gene leading to SVAS or Williams syndrome are identified by various techniques, including but not limited to, linkage analysis, fluorescent in situ hybridization (FISH), allele specific oligonucleotide (ASO) dot blot analysis, pulsed-field gel electrophoresis, Southern analysis, single-stranded conformation polymorphisms (SSCP), RNase protection assay and DNA sequencing of the variant genes. These techniques are also used for screening individuals for early identification of SVAS or Williams syndrome.

Diagnosis of SVAS and Williams syndrome can be made in some patients by noninvasive color flow Doppler echocardiography. Unfortunately, these studies are not completely sensitive or specific, especially in detecting peripheral pulmonary stenoses, which may be difficult to assess in larger patients (4, 43). Also, these techniques are only useful after the disease process is advanced. Invasive cardiac catheterization and angiography are more sensitive, especially in identification of peripheral pulmonary artery stenoses, but carry a significant risk of serious complications, and again are only useful after the disease had become manifest. The data described herein make diagnosis of SVAS and Williams syndrome definitive at, or even before, birth. The identification of the SVAS and Williams syndrome gene as the elastin gene by the linkage, translocation and mutations data makes genetic testing possible for additional families, including sporadic cases. Early, definitive diagnosis will benefit both affected and unaffected family members. Finally, the onset and magnitude of vascular obstruction caused by SVAS and Williams syndrome can be delayed by reducing the force of cardiac contraction, heart rate and blood pressure with pharmacologic agents.

Vascular disease is one of the more common causes of morbidity and mortality in industrialized societies. Over the last decade, a great deal has been learned about the environmental and metabolic causes of hypertension, hyperlipidemia, and diabetes, important vascular risk factors, but relatively little is known about additional genetic factors that play a role in vascular disease. SVAS and Williams syndrome offer important genetic clues about the pathogenesis of more common vascular disorders.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

1. Eisenberg, R., Young, D., Jacobson, B., Boito, A., Familial supravalvular aortic stenosis. *Am. J. Dis. Child.* 108, 341–7 (1964).

2. Grimm, T., Wesselhoeft, H., Zur genetik des Williams-Beuren-syndroms und der isolierten from der supravalvularen aortenstenose utersuccungen von 128 familien. *Zeitsch. Kardiol.* 69, 168–72 (1980).

3. Noonan, J. A., Syndromes associated with cardiac defects. Engle, M. A. (ed). Pediatric Cardiovascular Disease. Philadelphia: FA Davis Co. 97–116 (1981).

4. Morris, C. A., Demsey, S. A., Leonard, C. O., Dilts, C., Blackburn, B. L., Natural history of Williams syndrome: Physical characteristics. *J. Pediat.* 113, 318–26 (1988).

5. Chevers, N., Observations on the diseases of the orifice and valves of the aorta. *Guys. Hosp. Rep.* 7, 387–421 (1842).

6. O'Connor, W., Davis, J., Geissler, R., Cottrill, C., Noonan, J., Todd, E., Supravalvular aortic stenosis: clinical and pathologic observations in six patients. *Arch. Pathol. Lab. Med.* 109, 179–85 (1985).

7. Perou, M., Congenital supravalvular aortic stenosis. *Arch. Path.* 71, 113–26 (1961).

8. Pober, B. et al., Platelet-derived growth factor in supravalvular aortic stenosis of Williams syndrome. (Abstract). Williams Syndrome Association Professional Symposium 1990; Boston, Mass.

9. Jones, K. L., Williams syndrome: An historical perspective of its evolution, natural history, and etiology. *Am. J. Med. Genet.* 6, 89–96 (1990).

10. Friedman, W. F., Roberts, W. C., Vitamin D and the supravalvular aortic stenosis syndrome. The transplacental effects of vitamin D on the aorta of the rabbit. *Circ.* 34, 77–86 (1966).

11. Chan, G. M., Buchino, J. J., Mehlhorn, D, Bove, K. E., Steichen, J. J., Tsang, R. C., Effect of vitamin D on pregnant rabbits and their offspring. *Pediat. Res.* 13, 121–126 (1979).

12. Hitman, G. A., Garde, L., Daoud, W., Snodgrass, G. J., Cohen, R. D., The calcitonin-CGRP gene in the infantile hypercalcaemia/Williams-Beuren syndrome. *J. Med. Genet.* 26, 609–613 (1989).

13. Pastores, G. M., Michels, V. V., Schaid, D. J., Driscoll, D. J., Feldt, R. H., Thibodeau, S. N., Exclusion of calcitonin/ a-CGRP gene defect in a family with autosomal dominant supravalular aortic stenosis. *J. Med. Genet.* 29, 56–57 (1992).

14. Ensing, G. J., Schmidt, M. A., Hagler, D. J., Michels, V. V., Carter, G. A., Feldt, R. E., Spectrum of findings in a family with nonsyndromic autosomal dominant supravalvular aortic stenosis: a Doppler echocardiographic study. *JACC* 13, 413–9 (1989).

15. Tromp, G., Christiano, A., Indik, Z. et al., A to G polymorphism in ELN gene. *Nucl. Acids Res.* 19, 4314 (1991).

16. Tsui, L- C., Farrall, M., Report of the committee on the genetic constitution of chromosome 7. *Cytogenet. Cell. Genet.* 58, 337–81 (1991).

17. Merritt, A. D., Palmer, C. G., Lurie, P. R., Petry, E. L., Supravalvular aortic stenosis: genetic and clinical studies [Abstract.]. *J. Lab. & Clin. Med.* 62, 995 (1963).

18. Kahler, R. L., Braunwald, E., Plauth, W. H., Morrow, A. G., Familial congenital heart disease. *Am. J. Med.* 40, 384–99 (1966).

19. Hatle, L., Angelman, B., *Doppler ultrasound in cardiology: physical principles and clinical applications*. 1985; 2nd ed. Philadelphia: Lea & Febiger. 93.

20. Kunkel, L. M., Smith, K. D., Boyer, S. H., et al., Analysis of human Y-chromosomes-specific reiterated DNA in chromosome variants. *Proc. Nat. Acad. Sci. USA* 74, 1245–9 (1977).

21. Bell, G., Karem, J. H., & Rutter, W. J., Polymorphic DNA region adjacent to the 5' end of the human insulin gene. *Proc. Nat. Acad. Sci. USA* 78, 5759–63 (1981).

22. Southern, E. M., Detection of specific sequences among DNA fragments separated by gel electrophoresis. *J. Mol. Biol.* 98, 503–17 (1975).

23. Feinburg, A. P., & Vogelstein, B., Addendum: a technique for radiolabeling DNA restriction endonuclease fragments to high specific activity. *Anal. Biochem.* 137, 266–7 (1984).

24. Holm, T., Nakamura, Y., Ballard, L. et al., Isolation and mapping of a polymorphic DNA sequence (pTHH28) on chromosome 7p [D7S371]. *Nucl. Acids Res.* 16, 9887 (1988).

25. Dean, M., Stewart, C., Perry, A. et al., D7S448 detects a HindIII polymorphism located in the centromere region of chromosome 7. *Nucl. Acids Res.* 19, 200 (1991).

26. Lathrop, G. M., O'Connell, P., Leppert, M. et al. Twenty-five loci form a continuous linkage map of markers for human chromosome 7. *Genomics* 5, 866–73 (1989).

27. Lathrop, G. M., Lalouel, J. M., Julier, C., Ott, J., Strategies for multilocus linkage analysis in humans. *Proc. Nat. Acad. Sci. USA* 81, 3443–6 (1984).

28. Preus, M., The Williams syndrome: objective definition and diagnosis. *Clin. Genet.* 24, 433–8 (1984).

29. Fazio, M. J., Mattel, M- G., Passage, E. et al., Human elastin gene: New evidence for localization of/to the long arm of chromosome 7. *Am. J. Hum. Genet.* 48, 696–703 (1991).

30. Schwartz, D. C., and Cantor, C. R. (1984). Separation of yeast chromosome-sized DNAs by pulsed field gel electrophoresis. *Cell* 37, 67–75.

31. Saiki, R. K., Gelfand, D. H., Stoffel, S., Scharf, S. J., Higuchi, R., Horn, G. T., Mullins, K. B., and Erlich, H. A. (1988). Primer-directed enzymatic amplification of DNA with a thermostable DNA polymerase. *Science* 239, 487–491.

32. Benton, W. D., and Davis, R. W. (1977). Screening 1-gt recombinant clones by hybridization to single plaques in situ. *Science* 196, 180–182.

33. Indik, Z., Yoon, K., Morrow, S., Cicila, G., Rosenbloom, J., Rosenbloom, J., and Ornstein-Goldstein, N. (1987). Structure of the 3' region of the human elastin gene: great abundance of Alu repetitive sequences and few coding sequences. *Conn. Tis. Res.* 16, 197–211.

34. Fazio, M. J., Olsen, D., Kauh, E., Baldwin, C., Indik, Z., Ornstein-Goldstein, N., Yeh, H., Rosenbloom, J., and Uitto, J. (1988). Cloning of full-length elastin cDNAs from a human skin fibroblast recombinant cDNA library: further elucidation of alternative splicing utilizing exon-specific oligonucleotides. *J. Invest. Derm.* 91, 458–464.

35. Maniatis, T., Fritsch, E. F., and Sambrook, J. (1982). *Molecular Cloning: A Laboratory Manual* (Cold Spring Harbor, N.Y.: Cold Spring Harbor Laboratory), pp. 86–403.

36. Sanger, F., Nicklen, S., and Coulson, A. R. (1977). DNA sequencing with chain-terminating inhibitors. *Proc. Natl. Acad. Sci. USA* 74, 5463–5467.

37. Altschul, S. F., Gish, W., Miller, W., Myers, E. W., and Lipman, D. J. (1990). Basic local alignment search tool. *J. Mol. Biol.* 215: 403–410.

38. Indik, Z., Yeh, H., Ornstein-Goldstein, N., Sheppard, P., Anderson, N., Rosenbloom, J., Peltonen, L., and Rosenbloom, J. (1987). Alternative splicing of human elastin mRNA indicated by sequence analysis of cloned genomic and complementary DNA. *Proc. Natl. Acad. Sci. USA* 84, 5680–5684.

39. Bashir, M., Indik, Z., Yeh, H., Ornstein-Goldstein, N., Rosenbloom, J., Abrams, W., Fazio, M., Uitto, J., Rosenbloom, J. (1991). Characterization of the complete human elastin gene. *J. Biol. Chem.* 264: 8887–91.

40. Davidson, J. M. (1987). Elastin: structure and biology. In *Connective Tissue Disease: Molecular Pathology of the Extracellular Matrix*, J. Uitto and A. Perejda, eds. (New York, N.Y., Marcel Dekker), pp. 29–54.

41. Grimm, T., and Wesselhoeft, H. (1980). Zur genetik des Williams-Beuren-syndroms und der isolierten from der supravalvularen aortenstenose utersuccungen von 128 familien. *Zeitsche Kardiol.* 69, 168–172.

42. Morris, C. A. and Moore, C. A. (1991). The inheritance of Williams syndrome. *Proc. Greenwood Genet. Ctr.*, 10:81–82.

43. Chiarella, F., Bricarelli, F., Lupi, G., Bellotti, P., Domenicucci, S., Vecchio, C (1989). Familial supravalvular aortic stenosis: a genetic study. *J. Med. Genet.* 26, 86–92.

---

What is claimed is:

1. A method for determining whether Williams syndrome is present in a human, said method comprises determining a number of chromosomal copies of elastin gene present in said human's genome, the presence of only a single copy of said elastin gene being indicative that Williams syndrome is present in said human.

2. The method of claim 1 wherein said method is carried out by hybridization.

3. The method of claim 2 wherein said method is an in situ hybridization.

4. The method of claim 3 wherein said method is a fluorescent in situ hybridization.

* * * * *